US008173599B2

(12) United States Patent
Moon et al.

(10) Patent No.: US 8,173,599 B2
(45) Date of Patent: May 8, 2012

(54) SPRAY-DRIED COLLECTIN COMPOSITIONS AND PROCESS FOR PREPARING THE SAME

(75) Inventors: Hong Mo Moon, Englewood Cliffs, NJ (US); Jung Sun Yum, Kyonggi-do (KR); Byung Cheol Ahn, Yongin-Si (KR); Joo Youn Lee, Kyonggi-do (KR)

(73) Assignee: Dobeel Corporation, Jungwon-gu, Seongnam-si (KR)

( * ) Notice: Subject to any disclaimer, the term of this patent is extended or adjusted under 35 U.S.C. 154(b) by 822 days.

(21) Appl. No.: 11/436,377

(22) Filed: May 18, 2006

(65) Prior Publication Data

US 2007/0154406 A1 Jul. 5, 2007

Related U.S. Application Data

(63) Continuation of application No. PCT/KR2005/004682, filed on Dec. 30, 2005.

(30) Foreign Application Priority Data

Dec. 30, 2004 (KR) ........................ 10-2004-0117100

(51) Int. Cl.
*C07K 14/785* (2006.01)
*A61K 38/00* (2006.01)

(52) U.S. Cl. ........... 514/15.5; 514/2; 514/12; 424/278.1
(58) Field of Classification Search ........................ None
See application file for complete search history.

(56) References Cited

U.S. PATENT DOCUMENTS

| | | | | |
|---|---|---|---|---|
| 5,006,343 | A * | 4/1991 | Benson et al. | 424/450 |
| 5,270,199 | A * | 12/1993 | Ezekowitz | 435/372.1 |
| 5,464,649 | A * | 11/1995 | St. John et al. | 426/660 |
| 5,855,880 | A * | 1/1999 | Curtiss et al. | 424/93.2 |
| 5,883,084 | A * | 3/1999 | Peterson et al. | 514/78 |
| 6,315,983 | B1 * | 11/2001 | Eistetter | 424/45 |
| 6,429,192 | B1 * | 8/2002 | Laursen | 514/8 |
| 6,592,927 | B1 * | 7/2003 | Kruger et al. | 426/588 |
| 6,814,982 | B2 * | 11/2004 | Poncin et al. | 424/499 |
| 7,049,099 | B2 * | 5/2006 | Wakamiya | 435/69.6 |
| 7,332,470 | B2 * | 2/2008 | Fleiszig et al. | 514/2 |
| 2002/0193304 | A1 * | 12/2002 | Wada et al. | 514/12 |
| 2004/0247628 | A1 * | 12/2004 | Lintz et al. | 424/400 |
| 2004/0258705 | A1 * | 12/2004 | Zabrecky et al. | 424/185.1 |
| 2008/0214435 | A1 * | 9/2008 | Bonde | 514/2 |
| 2008/0242615 | A1 * | 10/2008 | Ikegami et al. | 514/12 |

FOREIGN PATENT DOCUMENTS

| | | | |
|---|---|---|---|
| KR | 20040106194 | A | 12/2004 |
| WO | WO 2004091436 | A2 * | 10/2004 |

OTHER PUBLICATIONS

NCBI (2008, updated) "Mannose-binding lectin", www.ncbi.nlm.nih.gov/entrez/viewer.fcgi?db=protein&id=47523054, pp. 1-2.*
NCBI (2008, updated) "Surfactant protein A", www.ncbi.nlm.nih.gov/entrez/viewer.fcgi?db=protein&id=118150792, pp. 1-2.*

Teera-Arunsiri et al. (2003) Preparation of spray-dried wettable powder formulations of *Bacillus thuringiensis*-based biopesticides, J. Econ. Entomol., vol. 96, No. 2, pp. 292-299.*

Rothmann et al. (1997) Structural characterization of bovine collectin-43, Eur. J. Biochem., vol. 243, No. 3, pp. 630-635.*

Van de Wetering et al. (2004) Collectins: players of the innate immune system, Eur. J. Biochem., vol. 271, No. 1, pp. 1229-1249.*

Loveles et al. (1995) Collectin-43 is a serum lectin with a distinct pattern of carbohydrate recognition, Immunology, vol. 85, No. 4, pp. 651-659.*

Tregoat et al. (2003) Dynamics of innate and cognitive immune components in human milk during lactation, J. Food Comp. Anal., vol. 16, pp. 57-66.*

Bharadwaj et al. (1999) A comparison of thermal characteristics and kinetic parameters of trehalases from a thermophilic and a mesophilic fungus, FEMS Microbiol. Lett., vol. 181, No. 1, pp. 187-193.*

Chien et al. (2006) Analysis of the health risk of exposure to breast milk mercury in infants in Taiwan, Chemosphere, vol. 64, No. 1, pp. 79-85.*

Wikipedia (2009, updated) Saline, http://en.wikipedia.org/wiki/Saline_(medicine), pp. 1-3.*

Pikal-Cleland et al. (2001) Lyophilization-induced protein denaturation in phosphate buffer systems: monomeric and tetrameric beta-galactosidase, J. Pharm. Sci., vol. 90, No. 9, pp. 1255-1268.*

(Continued)

*Primary Examiner* — Anand Desai
*Assistant Examiner* — Samuel Liu
(74) *Attorney, Agent, or Firm* — The Nath Law Group; Joshua B. Goldberg; Mihsuhn Koh

(57) ABSTRACT

The present invention relates to a spray-dried composition comprising as an active ingredient at least one member protein of the collectin family or its functional equivalent for treating and preventing microbial infectious diseases. The present invention also relates to a method for producing the same composition. The composition produced by the method of the present invention is effective in suppressing infections caused by viruses, bacteria, fungi, and parasites. Since the composition is developed in a form suitable for inhalation, it can directly provide the active ingredient to the sites of infection from these microbes, and thus treat and prevent respiratory infections and external wounds.

3 Claims, 26 Drawing Sheets

OTHER PUBLICATIONS

Sudmoon et al. (2008) Thermostable mannose-binding lectin from Dendrobium findleyanum with activities dependent on sulfhydryl content, Acta Biochim. Biophys. Sin (Shanghai), vol. 40, No. 9, pp. 811-818.*

Maa et al. (1998) Spray-Drying of Air_Liquid Interface Sensitive Recombinant Human Growth Hormone, J. Pharmaceu. Sci., vol. 87, No. 2, pp. 152-159.*

Hoppe, Hans-Jürgen et al., "Collectins—soluble proteins containing collagenous regions and lectin domains—and their roles in innate immunity", Protein Science, 1994, pp. 1143-1158, vol. 3, The Protein Society.

Hartshorn, Kevan L. et al., "Human Mannose-binding Protein Functions as an Opsonin for Influenza A Viruses", J. Clin. Invest., 1993, pp. 1414-1420, vol. 91, The American Society for Clinical Investigation, Inc.

Kase, T. et al., "Human mannan-binding lectin inhibits the infection of influenza A virus without complement". Immunology, 1999, pp. 385-392, vol. 97, Blackwell Science Ltd.

Ezekowitz, R. Alan B. et al., "A Human Serum Mannose-Binding Protein Inhibits In Vitro Infection By The Human Immunodeficiency Virus", J. Exp. Med., 1989, pp. 185-196, vol. 169. The Rockerfeller University Press.

Haurum, John S. et al., "Complement activation upon binding of mannan-binding protein to HIV envelope glycoproteins", AIDS, 1993, pp. 1307-1313, vol. 7, No. 10, Current Science Ltd.

Fischer, P.B. et al., "Mannan-Binding Protein and Bovine Conglutinin Mediate Enhancement of Herpes Simplex Virus Type 2 Infection in Mice", Scand. J. Immunol., 1994, pp. 439-445, vol. 39.

Ksiazek, Thomas G. et al., "A Novel Coronavirus Associated with Severe Acute Respiratory Syndrome", The New England Journal of Medicine, 2003, pp. 1953-1966, vol. 348, No. 20, Massachusetts Medical Society.

Peiris, J.S.M. et al., "Coronavirus as a possible cause of severe acute respiratory syndrome", The Lancet, 2003, pp. 1319-1325, vol. 361.

Neth, Olaf et al., "Mannose-Binding Lectin Binds to a Range of Clinically Relevant Microorganisms and Promotes Complement Deposition", Infection and Immunity, 2000, pp. 688-693, vol. 68, No. 2, American Society for Microbiology.

Van Emmerik, L.C. et al., "Binding of mannan-binding protein to various bacterial pathogens of meningitis", Clin. Exp. Immunol., 1994, pp. 411-416, vol. 97.

Tabona, P. et al., "Mannose binding protein is involved in first-line host defence: evidence from transgenic mice", Immunology, 1995, pp. 153-459, vol. 85.

Tregoat, Virginie et al., "Changes in the Mannan Binding Lectin (MBL) Concentration in Human Milk During Lactation", Journal of Clinical Laboratory Analysis, 2002, pp. 304-307, vol. 16, Wiley-Liss, Inc.

Wakamiya, Nobutaka et al., "Isolation and Characterization of Conglutinin as an Influenza A Virus Inhibitor", Biochemical and Biophysical Research Communications, 1992, pp. 1270-1278, vol. 187, No. 3, Academic Press, Inc.

Hartley, Carol A. et al., "Two Distinct Serum Mannose-Binding Lectins Functions as β Inhibitors of Influenza Virus: Identification of Bovine Serum β Inhibitor as Conglutinin", Journal of Virology, 1992, pp. 4358-4363, vol. 66, No. 7, American Society for Microbiology.

Reading, Patrick C. et al. "Collectin-Mediated Antiviral Host Defense of the Lung: Evidence from Influenza Virus Infection of Mice", Journal of Virology, 1997, pp. 8204-5212, vol. 71, No. 11, American Society for Microbiology.

Schwartz, Peter L. et al., "The Aggregation of [$^{125}$I] Human Growth Hormone in Response to Freezing and Thawing", Endocrinology, 1973, pp. 1795-1798, vol. 92, No. 6.

Koseki, Taihei et al., "Freezing Denaturation of Ovalbumin at Acid pH", J. Biochem., 1990, pp. 389-394, vol. 107, No. 3.

Broadhead, J. et al., "The Spray Drying of Pharmaceuticals", Drug Development and Industrial Pharmacy, 1992, pp. 1169-1206, vol. 18, Nos. 11 & 12, Marcel Dekker, Inc.

Labrude, P. et al., "Protective Effect of Sources on Spray Drying of Oxyhemoglobin", Journal of Pharmaceutical Sciences, 1989, pp. 223-229, vol. 78, No. 3, American Pharmaceutical Association.

Mumenthaler, Marco et al., "Feasibility Study on Spray-Drying Protein Pharmaceuticals: Recombinant Human Growth Hormone and Tissue-Type Plasminogen Activator", Pharmaceutical Research, 1994, pp. 12-20, vol. 11, No. 1, Plenum Publishing Corporation.

Bosquillon, Cynthia et al., "Pulmonary delivery of growth hormone using dry powders and visualization of its local fate in rats", Journal of Controlled Release, 2004, pp. 233-244, vol. 96, Elsevier B.V.

Chan, Hak-Kim et al., "Spray Dried Powders and Powder Blends of Recombinant Human Deoxyribonuclease (rhDNase) for Aerosol Delivery", Pharmaceutical Research, 1997, pp. 431-437, vol. 14, No. 4, Plenum Publishing Corporation.

Codrons, Valérie et al., "Systemic Delivery of Parathyroid Hormone (1-34) Using Inhalation Dry Powders in Rats", Journal of Pharmaceutical Sciences. 2003, pp. 938-950, vol. 92, No. 5, Wiley-Liss, Inc. and the American Pharmaceutical Association.

Maa, Yuh-Fun et al., "Spray-Drying Performance of a Bench-Top Spray Dryer for Protein Aerosol Powder Preparation", Biotechnology and Bioengineering, 1998, pp. 301-309, vol. 60, No. 3, John Wiley & Sons, Inc.

Maa, Yuh-Fun et al., "Effect of Spray Drying and Subsequent Processing Conditions on Residual Moisture Content and Physical/Biochemical Stability of Protein Inhalation Powders", Pharmaceutical Research, 1998, pp. 768-775, vol. 15, No. 5, Plenum Publishing Corporation.

Andya, James D. et al., "The Effect of Formulation Excipients on Protein Stability and Aerosol Performance of Spray-Dried Powders of a Recombinant Humanized Anti-IgE Monoclonal Antibody", Pharmaceutical Research, 1999, pp. 350-358, vol. 16, No. 3, Plenum Publishing Corporation.

Maa, Yuh-Fun et al., "The Effect of Operating and Formulation Variables on the Morphology of Spray-Dried Protein Particles", Pharmaceutical Development and Technology, 1997, pp. 213-223, vol. 2, No. 3, Marcel Dekker, Inc.

Anderson, O. et al., "Conglutinin Binds The HIV-1 Envelope Glycoprotein gp160 and Inhibits its Interaction with Cell Membrane CD4", Scand. J. Immunol., 1991, pp. 81-88, vol. 33.

Ushijima, Hiroshi et al., "Inhibition of Human Immunodeficiency Virus-1 Infection by Human Conglutinin-like Protein: In vitro Studies", Jpn. J. Cancer Res., 1992, pp. 458-464, vol. 83.

Zimmerman, P.E. et al., "120-kD Surface Glycoprotein of *Pneumocystis carinii* Is a Ligand for Surfactant Protein A", J. Clin. Invest., 1992, pp. 143-149, vol. 89, The American Society for Clinical Investigation, Inc.

Kuan, Shih-Fan et al., "Interactions of Surfactant Protein D with Bacterial Lipopolysaccharides. Surfactant Protein D is an *Escherichia coli*-Binding Protein in Bronchoalveolar Lavage", J. Clin. Invest., 1992, pp. 97-106, vol. 90, The American Society for Clinical Investigation, Inc.

* cited by examiner

SPRAY-DRIED COLLECTIN COMPOSITIONS AND PROCESS FOR PREPARING THE SAME

TECHNICAL FIELD

The present invention relates to a dry powder collectin composition which comprises one or more collecting. The present invention also relates to a method for preparing the dry powder collectin composition, especially a spray-dried powder composition suitable for pulmonary administration.

BACKGROUND OF THE INVENTION

Mannose-binding lectin ("MBL") is a mammalian serum protein which is involved in innate immunity against microbial infections. MBL recognizes the specific glycosylation patterns of the proteins on the cell surface of the infecting microorganism and binds to them to suppress the microbial infection according to three pathways described below. In the first pathway, MBL binds the microbial glycosylated protein to form a complex, and then activates MBL associated serine proteases ("MASPs"). The MASPs, in turn, cleave the second and fourth complement components ("C4" and "C2"), leading to an activation of the complement system. In the second pathway, MBL, bound to the glycosylated microbial cell surface proteins, serves as an opsonin and directs phagocytosis by neutrophils and macrophages. The same bound MBL can also neutralize the infectivity of the microbes in the third pathway, blocking their proliferation. Thus, the most important initial step in the MBL's defense against microbial infections is the recognition of and binding to the microbes.

MBL, a member of the collectin family, shares a common structure consisting of a collagen domain and a carbohydrate recognition domain (lectin domain) with other members of the family. The MBL monomer has a molecular weight of 32 kDa. It has a C-type carbohydrate recognition domain ("CRD") at the C-terminus, a cysteine-rich region at the N-terminus, and a collagen domain in-between. Three identical MBL monomeric polypeptides associate to form a triple helical complex through their collagen domains. By the disulfide bond formation of cysteines in the N-terminal region, up to six of the triple helical complex form oligomeric flower bouquet like molecules, consisting of dimmers, trimers, and so on to hexamers. This triple helix is a structural feature shared by all the collectin family members including surfactant proteins A ("SP-A") and D ("SP-D"), collectin-liver 1 ("CL-L1"), and collectin-placenta 1 ("CL-P1"). Thus, these member proteins belonging to the collectin family all share similar physicochemical properties. These collectin family proteins have been known to share another characteristic of playing an important role in the pre-immune defense against microbial infections in sera and the pulmonary surface as well (Hans-Jurgen et al, *Protein Science*, 3:1143, 1994). Besides the ones listed above, other family members include collectin-43 ("CL-43"), collectin-46 ("CL-46"), a bovine conglutinin, and a human conglutinin homolog.

MBL can bind to a wide range of oligosaccharides. As the target sugars are not normally exposed on mammalian cell surfaces at high densities, MBL does not usually recognize self-determinants, but is particularly well suited to interactions with microbial cell surfaces presenting repetitive carbohydrate determinants. MBL most often binds viruses with outer coats (viral envelopes). Representative examples include: influenza virus (Hartshorn, K. L. et al., *J. Clin. Invest.*, 91:1414, 1993; Kase, T. et al., *Immunol.*, 97:385, 1999), human immunodeficiency virus ("HIV") (Ezekowitz, R. A. et al, *J. Exp. Med.*, 169:185, 1989; Haurum, J. C. et al., *AIDS*, 7:1307, 1993), herpes virus (Fischer, C. B. et al., *Scan. J. Immunol.*, 39:439, 1994), and SARS corona virus (Ksiazek, T. G. et al., *N. Eng. J. Med.*, 348:1953, 2003; Peiris, J. S. M. et al., *Lancet*, 361:1319, 2003). Rhinoviruses, responsible for the common cold, are expected to be good binders to MBL as well. Among bacteria, *Staphylococcus aureus* (Neth, O. et al., *Infect. Immunol.*, 68:688, 2000) and *Hemophilus influenzae* (Van E. et al., *Clin. Exp. Immunol.*, 97:411, 1994) are reported to be good binders, whereas among fungi, *Candida albicans* (Tabona, P. et al., *Immunol.*, 85:153, 1995) is known to bind MBL.

Among the microbes that bind MBL, influenza virus, rhinovirus, severe acute respiratory syndrome ("SARS"), corona virus, and influenza virus of animal origin cause symptoms mainly through the infection of the respiratory epithelia, whereas *S. aureus* and *H. influenzae* infect lungs. *S. aureus* can also infect external wounds and *C. albicans* is involved in vaginitis. Since treating MBL in a solution phase is not suitable for curing these respiratory diseases and external wounds, special formulations are required. Although there have been many studies on MBL, the extent to which MBL is involved in the defense against the infections in epithelia and external wounds mentioned above is poorly understood. The only relevant study is one reporting a detection of MBL in saliva and breast milk (Tregoat, V. et al., *J. Clin. Lab. Anal.*, 16(6): 304, 2002).

Upon influenza virus infection, the virus proliferates in the epithelial cells that line the surfaces of respiratory organs. Once the virus has amplified itself inside the infected cell, new virus released from the cell infects neighboring epithelial cells. Thus, it is possible to disrupt contact between an epithelial cell and the virus using MBL which is capable of recognizing the glycosylated microbial surface proteins and binding to them. Thus, MBL binding to glycosylated flu virus surface protein, haemagglutinin and neuraminidase, blocks the new virus infection to the neighboring epithelial cells. In fact, it was observed in cultured cells that physical neutralization by MBL binding was sufficient for blocking microbial infection of neighboring cells. For example, MBL added to the culture medium prevented viral infection upon SARS corona virus inoculation of cultured cells (Korean patent gazette No. 1020040106194). Similar prevention of infection by MBL has been observed for influenza virus as well (Wakamiya, N. et al., *Biochem. Biophys. Res. Commun.*, 187:1270, 1992; Hartley, C. A. et al, *J. Virol.*, 66:4358, 1992; Patrick, C. R. et al., *J. Virol.*, 71:8204, 1997; Kase, T. et al., *Immunol.*, 97:385, 1999).

In order to treat external wounds and respiratory infections with MBL, it is desirable in many ways to formulate the protein into a powder. A powder formulation is capable of an effective delivery to sites of infection, delivers an optimal amount of MBL, lessens side effects due to its topical application, and reduces the amount used.

Freeze-drying and spray-drying are used in general to formulate protein drugs into powders. Freeze-drying is most widely employed nowadays. Freeze-drying is suitable for heat-sensitive proteins, but it is not suitable for producing a uniform powder with a diameter of a few micrometers, a form that can be readily inhaled. Freeze-drying also tends to concentrate proteins locally between the ice crystals while cooling. This local concentration brings about a rapid change in the pH and ionic strength surrounding the protein to cause protein denaturation and precipitation (Schwartz, P. L. et al., *Endocrinology*, 92(6): 1795, 1973; Koseki, T. et al., *J. Biochem.*, 107:389, 1990). In contrast, spray-drying involves spraying a continuous stream of a liquid sample to form microscopically dispersed droplets, while instantaneously drying them with hot air at the same time. Spray-drying has been in use for formulating various drugs. Spray-drying has the advantage of producing powders whose particle sizes are suitable for delivering drugs to respiratory tracts and lungs. Spray-drying also consumes less energy so that time and cost can be saved at the production line (Broadhead, J. et al., *Drug Dev. Ind. Pharm.*, 18(11&12):1169, 1992). Since proteins in general are not stable against heat, there are not many cases of protein drug formulations spray-dried with hot air. There are attempts, however, to apply spray-drying as follows: oxyhemoglobin (Labrude, P. et al., *J. Pharm. Sci.*, 78(3):223, 1989), human growth hormone (Mumenthaler, M. et al., *Pharm. Res.*, 11(1):12, 1994; Bosquillon, C., *J. Cont. Rel.*, 96:233, 2004), tissue plasminogen activator (Mumenthaler. M. et al., *Pharm. Res.*, 11(1): 12, 1994), DNase (Chan, H. K. et al., *Pharm. Res.*, 14(4):431, 1997), parathyroid hormone (Codrons, V. et al., *J. Pharm. Sci.*, 92(5):938, 2003), and humanized monoclonal antibody, anti-IgE, (Maa, Y. F. et al., *Biotechnol. Bioeng.*, 60(3):301, 1998).

Especially when producing spray-dried protein compositions for respiratory applications, it is desirable to formulate proteins into powders with particle sizes of 5 μm or less. The particle size, shape and water content of such powders are important factors in terms of treatment efficacy (Hickey, A. J. et al., *Pharm. Tech.*, 18:58, 1994). The major determinants of the physical characteristics of such powders are mechanical conditions such as the feed velocities for hot air and the protein solution, temperature and spray pressure (Maa, Y. F. et al., *Pharm. Res.*, 15(5):768, 1998) as well as the identities and concentrations of the excipients to the protein solution such as salts, sugars, and proteins (Andya, J. D. et al., *Pharm. Res.*, 16(3):350, 1999; Maa, Y. F. et al., *Pharm. Dev. Tech.*, 2(3): 213, 1997). Also in the dry powder formulation of recombinant human MBL by spray-drying, the important considerations are that a spray-dried MBL powder composition should maintain its ability to activate complement through the specific binding to the glycosylated, MBL-binding proteins in the presence of serine proteases when dissolved and that such ability is also not lost during long-term storage.

However, there have been no studies reported on spray-drying methods for producing powder collectin composition in general, human recombinant MBL compositions in particular, for treating illnesses such as respiratory inflammation. Thus, there is a strong need for spray-drying methods to produce a dry powder collectin composition available for respiratory inhalation and application to external wounds. Accordingly, the present invention provides a dry powder collectin composition formed by adding a carbohydrate and/or protein excipients to a solution containing at least one collectin family member protein and spray-drying the solution. This powder is able to support long-term storage without losing its efficacy.

SUMMARY OF THE INVENTION

The present invention provides a dry powder collectin composition which comprises one or more collectins, and one or more excipients selected from the group consisting of tonicity enhancing agents, divalent ion salts, protein excipients, carbohydrates, and polymer excipient, for enhancing the particle physical characteristics, and pharmacological and biological properties of the composition. In particular, the dry powder collectin composition is a spray-dried collectin composition with a particle size ranging from 1 to 5 μm, which is aerosolizable for inhalation to treat or prevent respiratory infections. The spray-dried collectin composition can also be administered directly to other cavities and sites of microbial infection on the surface for treatment and/or prevention of such infections. Suitable divalent ion salt may contain calcium cation, which may be important for the biological activities of the collectins selected.

The present invention also provides a method for producing the dry powder collectin composition, which comprises the steps of preparing an aqueous solution or suspension which comprises the active components (i.e., one or more collectins) and spray-drying the collectin solution to form a spray-dried collectin composition. The collectin solution may also include a divalent cation and/or pharmaceutically acceptable excipients. By varying each individual component in the collectin solution, an aerosolizable spray-dried collectin composition is produced with particle sizes and a particle size distribution suitable for respiratory inhalation. The method may further comprise a sterilization step, preferably prior to the spray drying step, for removing endotoxins and/or microbes to produce a sterile collectin composition.

BRIEF DESCRIPTION OF THE DRAWINGS

FIGS. 4 A-E compare the C4 activation levels of spray-dried MBL powder compositions (open circles) produced at five different temperature settings: 80° C./58° C.

DETAILED DESCRIPTION OF THE INVENTION

Figure 1:
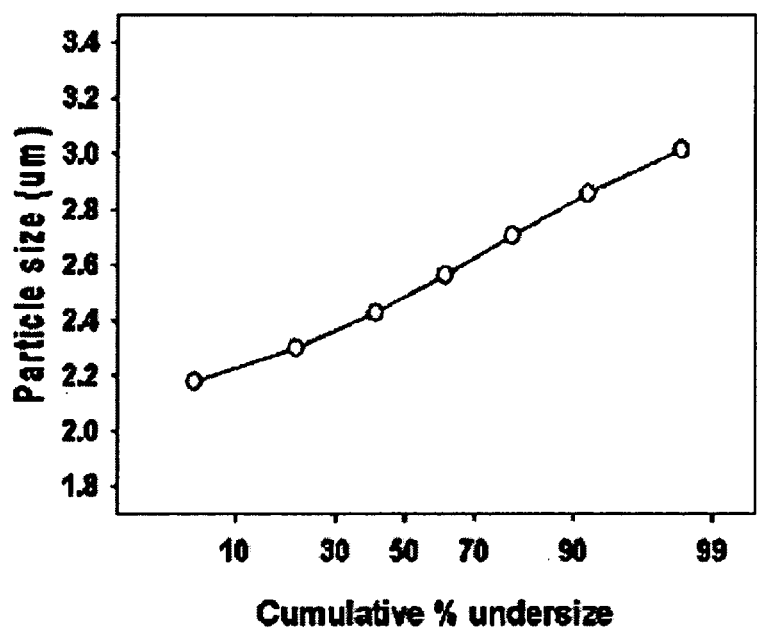
FIG. 1 shows the particle size distribution for a spray-dried MBL powder composition which contains sucrose and casein.

As used in this disclosure, the singular forms "a", "an", and "the" may refer to plural articles unless specifically stated otherwise. Thus, for example, a reference to a composition which comprises a collectin is intended to include a plurality of collecting. Furthermore, the use of grammatical equivalents of articles such as "protein" or "polypeptide" is not meant to imply differences among these terms unless specifically indicated in the context.

Unless defined otherwise, all technical and scientific terms used herein generally have the same meaning as commonly understood by one of ordinary skill in the art to which this invention belongs. Generally, the nomenclature used herein and the laboratory procedures in biochemistry, biology, immunology, and pharmacology described herein are those well known and commonly employed in the art.

To facilitate understanding of the invention set forth in the disclosure that follows, a number of abbreviations and ten-s are defined below.

Definition

The term "MBL" refers to mannose-binding lectin, which is also known as mannan-binding lectin, and mannan-binding protein or mannose-binding protein ("MBP").

The term "MASP" refers to an MBL associated serine protease.

The term "C2" refers to the second complement component.

The term "C4" refers to the fourth complement component.

The term "CRD" refers to a carbohydrate recognition domain.

The term "SP-A" refers to surfactant protein A.
The term "SP-D" refers to surfactant protein D.
The term "CL-L1" refers to collectin-liver 1.
The term "CL-P1" refers to collectin-placenta 1.
The term "CL-43" refers to collectin-43.
The term "CL" refers to collectin.

The terms "effective amount" and "therapeutically effective amount" each refer to the amount of a collectin molecule used to support an observable level of one or more biological activities of the collectin as set forth herein.

The term "functional equivalent" refers to a polypeptide which does not have the exact same amino acid sequence of a naturally occurring collectin protein, due to alternative splicing, deletions, mutations, additions, or chemical modifications, but retains at least about 1%, at least about 10%, at least about 25%, at least about 50%, or at least about 70% of the biological activity of the naturally occurring collectin. As used herein, unless otherwise indicated, the term "collectin" refers to a collectin and functional equivalents thereof.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "pharmaceutically acceptable carrier" or "physiologically acceptable carrier" refers to one or more formulation materials suitable for accomplishing or enhancing the delivery of the collectin as a pharmaceutical composition.

The term "residual activity" refers to a relative activity of a collectin sample in comparison with its collectin control. For processing stability, the collectin control is usually the collectin solution from which the dry powder collectin composition is produced. For storage stability, the collectin control is usually the same dry powder collectin composition but stored at room temperature. In general, a residual activity of a collectin composition is expressed as a percentage of the activity of the collectin control.

Collectin

Collectins are a family of collagenous calcium-dependent defense lectins which have been found in various mammals, including humans, rodents, cattle, cows, pigs, chickens, and mice. Their polypeptide chains are composed of four distinct domains: a cystein-rich N-terminal domain, a collagen domain, and .alpha.-helical coiled-coil neck domain, and a C-terminal lectin domain or carbohydrate recognition domains ("CRD"). Some well characterized collectins include mannan-binding lectin ("MBL"), surfactant protein A ("SP-A"), surfactant protein D ("SP-D"), collectin liver 1 ("CL-L1"), collectin placenta 1("CL-P1"), conglutinin, collectin of 43 kDa ("CL-43"), and collectin of 46 kDa ("CL-46").

The collectins of the present invention may come from any species. The collectin may be in a native form purified from natural sources or in a recombinant form produced using protein engineering technologies, which may have different post-translation modification from the native collectin. These native and recombinant collectin proteins can be obtained commercially or produced readily with recombinant vectors by standard molecular biology protocols well-known to those skilled in the art; e.g., human CL-P1 is available as a recombinant protein from R&D systems (Minneapolis, Minn., USA).

The collectins of the present invention may also be biologically active collectin variants. Unless otherwise indicated, the term "collectin" refers both to native collecting, as well as variants thereof. As used herein, a collectin variant is a collectin protein which comprises an amino acid sequence having one or more amino acid substitutions, deletions, and/or additions (such as internal additions and/or collectin fusion proteins) as compared to the amino acid sequence of a native collectin. Variants may be naturally occurring (e.g., collectin polypeptide allelic variants, collectin polypeptide orthologs, and collectin polypeptide splice variants) or artificially constructed. Such collectin variants may be prepared from the corresponding nucleic acid molecules having a DNA sequence that varies accordingly.

The variants may have from 1 to 3, to 5, to 10, to 15, to 20, to 25, to 50, to 75, or to 100, or more than 100 amino acid substitutions, insertions, additions and/or deletions, wherein the substitutions may be conservative, or non-conservative, or a combination thereof. Additionally, the collectin of the present invention may comprise at least 10, at least 12, at least 15, at least 20, at least 25, at least 30, at least 35, at least 40, or at least 50 consecutive amino acid residues of a native collectin. Such a variant is preferably at least about 50%, at least about 60%, at least about 70%, at least about 80%, as lest about 90%, or at least about 95% identical to a native collectin. Furthermore, the collectin variant is biologically active with an activity of over about 1%, over about 10%, over about 25%, over about 50%, over about 60%, over about 70%, over about 80%, over about 90%, over about 95%, or over about 100% of the activity of a native collectin.

Conservative modifications to the amino acid sequence of a collectin generally produce a polypeptide having functional and chemical characteristics similar to those of the original collectin protein. In contrast, substantial modifications in the functional and/or chemical characteristics of a collectin may be accomplished by selecting substitutions in the amino acid sequence of the collectin that differ significantly in their effects on maintaining (a) the structure (secondary, tertiary, and/or quandary) in the area of the substitution or (b) the charge or hydrophobicity of the molecule at the target site. Amino acid sequence modifications can be accomplished by chemical and biological peptide and protein synthetic methods that are well know in the art.

Desired amino acid substitutions (whether conservative or non-conservative) can be determined by those skilled in the art at the time such substitutions are required. For example, amino acid substitutions can be used to identify important residues, to modulate the biological activity of a collectin, or to decrease unwanted side effects associated with a collectin when used as a therapeutic agent. Suitable amino acid substitutions include, but are not limited to, substituting Ala with Val, Leu, or Ile; substituting Arg with Lys, Gln, or Asn; substituting Asn with Gln; substituting Asp with Glu; substituting Cys with Ser or Ala; substituting Gln with Asn; substituting Glu with Asp; substituting His with Asn, Gln, Lys, or Arg; substituting Ile with Leu, Val, Met, Ala, Phe, or Norleucine; substituting Leu with Norleucine, Ile, Val, Met, Ala, or Phe; substituting Lys with Arg, 1,4-diamino-butyric acid, Gln, or Asn; substituting Met with Leu, Phe, or Ile; substituting Phe with Leu, Val, Ile, Ala, or Tyr; substituting Pro with Ala; substituting Ser with Thr, Ala, or Cys; substituting Thr with Ser; substituting Trp with Tyr or Phe; substituting Tyr with Trp, Phe, Thr, or Ser; and substituting Val with Ile, Met, Leu, Phe, Ala, or Norleucine. The selection of an amino acid for replacement can also be guided by its hydropathic index and/or hydrophilicity.

In addition, the collectin polypeptide may be fused to a homologous polypeptide to form a homodimer or to a heterologous polypeptide to form a heterodimer. Heterologous polypeptides include, but are not limited to: an epitope to allow for the detection and/or isolation of a collectin fusion polypeptide; an enzyme or portion thereof which is catalytically active; a polypeptide which promotes oligomerization, such as a leucine zipper domain; a polypeptide which increases stability, such as an immunoglobulin constant region; and a polypeptide which has a therapeutic activity different from the collectin polypeptide.

Fusions can be made either at the amino-terminus or at the carboxyl-terminus of a collectin polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a protease to allow for the separation of the fused moieties. It will be appreciated that once constructed, the fusion polypeptides can further be derivatized according to the methods described herein.

The collectin of the present invention may also be a collectin derivative, which is a chemically modified collectin, including protein post-translation modification, such as acylation (i.e., acetylation or formylation), biotinylation, carboxylation, deamination, glutathionylation, glycosylation, lipidation (i.e., farnesylation, gernylgeranylation, prenylation, myristoylation, palmitoylation, or stearoylation), methylation, phosphorylation, sulphation, and ubiquitination. Unless otherwise indicated, the term "collectin" refers both to native collectins as well as derivatives thereof. A collectin derivative may be modified in a manner that is different in the type, number, or location of the post-translation modification groups naturally attached to the polypeptide. For example, a collectin derivative may have the number and/or type of glycosylation altered compared to the native collectin. The resulting collectin derivative may comprise a greater or a lesser number of N-linked glycosylation sites than the native collectin.

The collectin polypeptide may also be modified by the covalent attachment of one or more polymers. Typically, the polymer selected is water-soluble so that the protein to which it is attached does not precipitate in an aqueous environment, such as a physiological environment. The polymer may be of any molecular weight and may be branched or unbranched. The polymer each typically has an average molecular weight of between about 1 kDa to about 100 kDa.

Suitable water-soluble polymers or mixtures thereof include, but are not limited to, polyalkylene glycol (such as mono-($C_1$-$C_{10}$) alkoxy-, aryloxy-polyethylene glycol, poly-(N-vinyl pyrrolidone) polyethylene glycol, propylene glycol homopolymers, or polypropylene oxide/ethylene oxide copolymers), carbohydrate-based polymers (such as dextran or cellulose), polyoxyethylated polyols, and polyvinyl alcohols. Also encompassed by the present invention are bifunctional crosslinking molecules which can be used to prepare covalently attached collectin polypeptide multimers.

In general, chemical derivatization may be performed under a suitable condition by reacting a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby a collectin becomes attached to one or more polymer molecules, and (b) obtaining the reaction products. The optimal reaction conditions may vary depending upon the collectin selected and chemical reagents used, and are generally determined experimentally. The PEGylation of a polypeptide may be carried out using any of the PEGylation reactions known in the art, including, but not limited to, acylation, alkylation, or Michael addition.

Dry Powder Collectin Composition

The dry powder collectin composition of the present invention comprises one or more collecting. As used herein, unless otherwise indicated, the term "collectin" refers to collectins and functional equivalents thereof. Particularly, a functional equivalent of a collectin, as used herein, encompasses a collectin variant or derivative described hereinabove, which possess substantially biological activity of the original collectin. As a therapeutic agent, the active component in the dry powder collectin composition is the collectin contained in the composition. The active component of the collectin composition may be a collagenous protein which has a CRD domain and collagen domain. More specifically, the active component may be a collectin protein selected from the group consisting of MBL, SP-A, SP-D, CL-L1, CL-P1, conglutinin, CL-43, CL-46, and functional equivalents thereof. Representatively suitable for use in the methods and compositions described herein are MBL and its functional equivalents. For example, the active component in the dry powder collectin composition is a recombinant MBL, which is produced from the cell line of accession number KCTC 10472BP (Korean patent gazette No. 1020040106194).

The dry powder collectin composition may also contain a divalent cation, such as magnesium ($Mg^{2+}$), zinc ($Zn^{2+}$), or calcium ($Ca^{2+}$), which may be desired for the activation of the complement system for a collectin. Typically, a calcium ion is provided as a calcium salt, both organic and inorganic, with a sufficient water solubility. Suitable calcium salts include, but are not limited to, calcium chloride, calcium bromide, calcium iodide, calcium sulfate, and calcium nitrate, tricalcium citrate, calcium lactate, and calcium gluconate.

In addition, dry powder collectin composition may further comprise pharmaceutically acceptable excipients for modifying, maintaining, or preserving, for example, the pH, osmolarity, viscosity, clarity, color, isotonicity, odor, sterility, stability, rate of dissolution or release, adsorption, or penetration of the collectin composition.

Suitable pharmaceutical excipients include, for example, amino acids and low molecular weight polypeptides, antimicrobials, antioxidants (such as ascorbic acid, sodium sulfite, or sodium hydrogen-sulfite), antistatic agents, buffers (such as borate, bicarbonate, Tris-HCl, citrates, phosphates, or other organic acids and bases), bulking agents (such as mannitol or glycine), chelating agents (such as EDTA), complexing agents (such as caffeine, polyvinylpyrrolidone, beta-cyclodextrin, or hydroxypropyl-beta-cyclodextrin), fillers, carbohydrates, proteins (such as albumins, gelatin, casein, hemoglobin, and immunoglobulins), coloring, flavoring and diluting agents, emulsifying agents, hydrophilic polymers (such as polyvinylpyrrolidone), preservatives (such as benzalkonium chloride, benzoic acid, salicylic acid, thimerosal, phenethyl alcohol, methylparaben, propylparaben, chlorhexidine, sorbic acid, or hydrogen peroxide), polyols (such as glycerin, propylene glycol, polyethylene glycol, mannitol, or sorbitol), polymers, suspending agents, surfactants or wetting agents (such as pluronics, PEG, sorbitan esters, polysorbates, Triton, tromethamine, lecithin, cholesterol, or tyloxapal), stability enhancing agents (such as sucrose or sorbitol), taste-masking agents, tonicity enhancing agents (such as alkali metal halides, sodium chloride, potassium chloride, or mannitol sorbitol), and pharmaceutical adjuvants (*Remington's Pharmaceutical Sciences*, 18th Ed., A. R. Gennaro, ed., Mack Publishing Company 1990; *Handbook of Pharmaceutical Excipients*, 3rd Ed., Kibbe, A. H. Editor 2000).

Non-limiting exemplary amino acid excipients include glycine (Gly), alanine (Ala), valine (Val), norvaline (2-aminopentanoic acid), 2-aminoheptanoic acid, leucine (Leu), isoleucine (Ile), methionine (Met), proline (Pro), phenylalanine (Phe), trytophan (Trp), serine (Ser), threonine (Thr), cysteine (Cys), tyrosine (Tyr), asparagine (Asp), glutamic acid (Glu), lysine (Lys), arginine (Arg), histidine (His), and norleucine (Nor). Non-limiting exemplary polypeptide excipients include oligomers comprising 2-9 amino acids and preferably 2-5 amino acids, all of which may be homo or hetero species.

Non-limiting exemplary carbohydrate excipients include, but are not limited to, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, and myoinositol.

Generally, the dry powder collectin composition of the present invention contains from about 0.01% to about 99.999%, from about 1% to about 99%, or from about 5 to about 80% by weight excipients in total. Generally, the optimal amount of each excipient is determined experimentally, i.e., by preparing a series of collectin-containing compositions containing varying amounts of each excipient, examining the biological, chemical, and physical properties of the resulting collectin powder, then further exploring the range at which optimal aerosol performance is attained with no significant deleterious effects upon these properties and storage stability.

In one embodiment, the dry powder collectin composition may also comprise a divalent cation salt, such as calcium chloride, and optionally a tonicity enhancing agent such as sodium chloride. In the dry powder collectin composition, the content of active components in total may range from about 0.001 to 90 parts, from about 0.001 to about 60 parts, or from about 0.01 to about 60 parts by weight; the content of the divalent cation salt may range from about 0.1 to about 90 parts or from about 0.1 to about 10 parts by weight; and the content of tonicity enhancing agent may range from about 0.1 to about 10 parts by weight.

In yet another embodiment, the dry powder collectin composition may further comprise a carbohydrate excipient, such as lactose or sucrose. The carbohydrate content may range from about 5 to about 80 parts by weight.

In certain embodiments, the dry powder collectin composition may also comprise a protein excipient (such as casein) and optionally an organic polymer excipient such as polyvinyl alcohol ("PVA"). The content of the protein excipient may range from about 0.1 to about 94 parts or from about 0.1 to about 20 parts by weight and the content of the organic polymer may range about 0.001 to about 10 parts by weight.

In a particular embodiment, the active component of the dry powder collectin composition is MBL. The collectin composition comprises MBL of from about 0.001 to about 60 parts, sodium chloride of from about 0.1 to about 10 parts, $CaCl_2$ from about 0.1 to about 10 parts, and a carbohydrate of about 5 to about 80 parts by weight.

In another particular embodiment, the dry powder collectin composition comprises MBL of from about 0.001 to about 0.1 parts, sodium chloride of from about 8 to about 9 parts, $CaCl_2$ from about 1 to about 2 parts, a carbohydrate of about 20 parts, and PVA of about 0.5 parts by weight. The active component, MBL, may be isolated from a natural source or produced recombinantly.

The numerical values of parts above refer to a weight ratio of the constituents forming the dry powder composition. When the dry powder composition of the present invention is prepared from an aqueous solution and all the solutes are non-volatile, it is evident that the ratio of solutes by weight will be maintained in the final dry powder composition. Thus, molarities and weight per volume percents are readily converted to parts by weight; for example, 10 mM $CaCl_2$ (molecular weight 111) corresponds to $10 \times 10^{-3} \times 111 = 1.11$ parts by weight.

Furthermore, the dry powder collectin composition may have residual moisture content of below about 20%, below about 10%, below about 6% by weight, below about 3%, below about 2%, or between about 0.5 and 2% by weight. Such low moisture-containing solids tend to exhibit a greater stability upon packaging and storage. Generally, the dry powder collectin composition of the present invention is hygroscopic, i.e., it demonstrates a tendency to absorb moisture from the atmosphere if not stored in sealed containers such as blister packages.

According to the present invention, the particles of the dry powder collectin composition may have various sizes, shapes, and particle size distribution. These particle physical characteristics are affected by both the types and amounts of the active component and pharmaceutically acceptable excipients contained in the composition. The particles may have a mass median diameter ("MMD") of less than about 20 µm, less than about 10 µm, less than about 7.5 µm, less than about 5 µm, less than about 4 µm, or less than about 3.5 µm, and are usually in the range of about 0.1 µm to about 5 µm, about 1 µm to about 5 µm, about 0.1 µm to about 4 µm, about 1.5 µm to about 4.5 µm, about 2 µm to about 4 µm, or about 2.5 µm to about 3.5 µm in diameter for effective pulmonary administration. In some embodiments, the powder may also contain non-respirable carrier particles such as lactose, where the non-respirable particles are typically greater than about 40 microns in size.

In the present invention, the particle size distribution of the dry powder collectin composition depends on the excipients in the composition. Typically, the particle sizes range from about 1 to about 10 µm. For inhalation into deep lung, the suitable particle sizes are smaller than about 5 µm, typically ranging from about 1 to about 4 µm.

The dry powder collectin composition of the present invention possesses both processing stability and storage stability. As used herein, processing stability is a measure of the ability of a protein to retain its biological activity during processing, such as spray-drying or lyophilization process, and expressed as a residual activity in comparison to that of the original collectin solution from which the dry powder is prepared. The processing stability is expressed in a residual activity by comparing the biological activities of the active components prior to and after being processed. The active component, which comprises one or more collectins as described hereinabove, in the dry powder collectin composition has no less than about 50%, no less than about 60%, no less than about 70%, no less than about 80%, no less than about 85%, no less than about 90%, no less than about 95%, no less than about 97%, no less than about 98%, or no less than about 99% of the biological activity of the collectin in solution or suspension, from which the dry powder composition is produced. The biological activity of a collectin composition can be accessed by the biological assays well known in the art, such as a functional ELISA assay. For example, the MBL activity can be readily measured using a assay such as a human MBL-C4 activation complex ELISA assay as described herein in details in the example section.

The dry powder collectin composition of the present invention also exhibits good storage stability, as characterized by its ability to retain the biological activities of its active components upon storage. The storage stability is determined under stress conditions that correspond to one year-long storage under ambient conditions (25° C. and ambient humidity). The two stress conditions employed in the present invention are 60° C. for 4 days or 70° C. for 2 days at a relative atmospheric humidity of 2%. These conditions are known to be equivalent to one year-long storage. The composition is then analyzed for biological activity using suitable methods, such as a functional enzyme-linked immunosorbent assay ("ELISA"). The dry powder collectin composition of the present invention is stable for at least about 3 months, at least about 6 months, at least about 9 months, at least about 12 months, at least about 15 months, at least about 18 months, at least about 21 months, at least about 24 month, or at least about 30 months, when stored at room temperature and under ambient humidity. After storage at room temperature and ambient humidity for a year or equivalent conditions, the active component in the dry powder collectin composition possesses at least about 50%, at least about 60%, at least about 70%, at least about 80%, at least about 85%, at least about 90%, at least about. 95%, at least about 97%, at least about 98%, or at least about 99% of the biological activity of the active component prior to storage.

As described below, the dry powder collectin composition of the present invention may be prepared using a spray drying process. The dry powder collectin composition thus produced is a spray-dried collectin powder composition, which is aerosolizable for an effective inhalation to the lung and respiratory tracts. The dry powder collectin composition may also be produced by other known methods, such as lyophilization or freeze-drying.

Method for Preparing Dry Powder Collectin Composition

The dry powder collectin composition of the present invention may be prepared by spray drying under conditions which minimize the extent of protein denaturalization and aggregation. Some general spray drying processes can be found in "Spray Drying Handbook", 5th ed., K. Masters, John Wiley & Sons, Inc., NY, N.Y. (1991). In general, the dry powder collectin composition is spray dried from an aqueous solution or suspension, depending upon factors such as the solubility and stability of the active components at the pH range employed. In a specific embodiment, the active component, such as recombinant MBL, is first dissolved in water or a physiologically acceptable buffer such as Ringer solution, at a pH of from about 3 to 11, from about 4 to about 10, from about 5 to about 9, from about 5.5 to about 8.5, from about 6 to about 8, or from about 6.5 to about 7.5. For pulmonary delivery, a neutral pH, which is between about 5.5 and about 7.8, is suitable since such pH may aid in maintaining the physiological compatibility of the powder after dissolution of powder within the lung.

The aqueous formulation may optionally contain additional water-miscible solvents, such as acetone, alcohols, and acetonitrile. Representative alcohols are lower alcohols such as methanol, ethanol, propanol, and isopropanol. Such mixed solvent systems may typically contain no greater than about 80%, from about 20% to about 40%, or from about 10% to about 30% by volume of a water miscible solvent.

The pre-spray-dried solution generally contains solids dissolved at a concentration of from about 0.01% to about 20% (weight/volume), from about 0.05% to about 10% (weight/volume), or from about 0.1% to about 2% (weight/volume). Weight per volume (w/v) may also be expressed as mg/mL, for example, 1% weight/volume is equivalent to 10 mg/mL. Specifically, the pre-spray dried solution may typically possess one of the following solids concentrations: 0.1 mg/mL or greater, 0.5 mg/mL or greater, 1 mg/mL or greater, 1.5 mg/mL or greater, 2 mg/mL or greater, 3 mg/mL or greater, 4 mg/mL or greater, or 5 mg/mL or greater. The total concentration of the active components in the pre-spray dried solution may range from about 1 ng/mL to about 100 mg/mL, from about 100 ng/mL to about 10 mg/mL, from about 1 µg/mL to about 100 µg/mL, from about 1 µg/mL to about 50 µg/mL, from about 1 µg/mL to about 20 µg/mL, or about 1 µg/mL to about 10 µg/m L.

In an exemplary embodiment, the pre-spray-dried solution comprises an active component at a concentration of from 0.0005 to about 10% (w/v), a carbohydrate at a concentration from about 0.1 to about 4% (w/v), and optionally a tonicity enhancing agent and a divalent cation salt, each at a concentration of from about 0.01 to about 10% (w/v). In another exemplary embodiment, the pre-spray dried solution may further comprises a protein excipient such as casein at a concentration of from about 0.005 to about 0.2% (w/v) and optionally a polymer excipient, such as PVA, at a concentration of from 0.001 to about 10% (w/v).

The solution can be spray dried in a conventional spray drier, such as those available from commercial suppliers such as LaPlant SD-05 (UK), Niro A/S (Denmark), and Buchi (Switzerland), resulting in a dispersible dry powder. Optimal conditions for spray drying the solution may vary depending upon the formulation components, and are generally determined experimentally. The gas used to spray dry the solution is typically air, although inert gases such as nitrogen or argon are also suitable. Moreover, the temperature of both the inlet and outlet of the gas used to dry the sprayed solution is such that it does not cause decomposition and denaturalization of the active component in the sprayed solution. Such temperatures are typically determined experimentally, although generally, the inlet temperature may range from about 50° C. to about 200° C., while the outlet temperature may range from about 30° C. to about 150° C.

Suitable temperatures for the inlet gas may range from about 50 to about 220° C., to about 150° C., to about 120° C., to about 110° C., to about 105° C., or to about 100° C.; from about 60 to about 220° C., to about 150° C., to about 120° C., to about 110° C., to about 105° C., or to about 100° C.; from about 70 to about 220° C., to about 150° C., to about 120° C., to about 110° C., to about 105° C., or to about 100° C.; from about 80 to about 220° C., to about 150° C., to about 120° C., to about 110° C., to about 105° C., or to about 100° C. Representatively suitable temperatures for the inlet gas may be about 85° C., about 90° C., about 95° C., or about 100° C.

Suitable temperature for the outlet air or discharge temperatures may range from about 40 to about 150° C., to about 100° C., to about 90° C., to about 80° C., to about 75° C., or to about 70° C.; from about 50 to about 150° C., to about 100° C., to about 90° C., to about 80° C., to about 75° C., or to about 70° C.; from about 60 to about 150° C., to about 100° C., to about 90° C., to about 80° C., to about 75° C., and to about 70° C.; about 55° C., about 60° C., about 65° C., or about 70° C.

Preferably, the spray drying process is operated with a sufficient atomization pressure to maintain a suitable spraying rate and a suitable hot air flow rate. Suitable spraying rates may range from about 500 to 2000 liter per hour (L/h), whereas suitable hot air flow rates may range from about 400 to about 1,200 L/min. Atomization pressures may range from about 20-150 psi or from about 30-40 to 100 psi. Typically, the atomization pressure employed may be one of the following (psi): 20, 30, 40, 50, 60, 70, 80, 90, 100, 110, 120 or above. Spray dried powders are physically distinct from powders prepared by other evaporative drying methods, such as lyophilization and air drying, and typically exhibit morphologies and thermal histories (including glass transition temperatures, glass transition widths, and enthalpic relaxation profiles) that differ from those of powders prepared by other drying methods.

The method may further comprise a sterilization step for removing endotoxins and/or microbes to produce a sterile collectin solution prior to drying process. This may be accomplished, for example, by filtration through sterile filtration membranes. Once formed, the dry powder collectin composition is typically maintained under dry (i.e., relatively low humidity, such as, less than 30% moisture) conditions during manufacture, processing, and storage.

Administration of Dry Powder Collectin Composition

The present invention also provides a pharmaceutical formulation which comprises the dry powder collectin composition as described above. The dry powder collectin composition of the present invention is suitable for administration via any route known to be effective by the physician of ordinary skill. The dry powder collectin composition can be formulated into any pharmaceutical formulation in accordance with conventional methods of pharmacy to produce medicinal agents for administration to patients, including humans and other mammals.

In one embodiment, the dry powder collectin composition is delivered through pulmonary route of administration. This is particularly suitable for the spray-dried collectin composition of the present invention due to their particle sizes and particle size distribution profiles. The dry powder collectin composition may be delivered using any suitable dry powder inhaler ("DPI"), i.e., an inhaler device that utilizes the patient's inhaled breath as a vehicle to transport the dry powder drug to the lungs. When administered using a device of this type, the powder is contained in a receptacle having a puncturable lid or other access surface, preferably a blister package or cartridge, where the receptable may contain a single dosage unit or multiple dosage units.

The dry powder collectin composition may also be delivered using a pressurized, metered dose inhaler ("MDI"), containing a solution or suspension of drug in a pharmaceutically inert liquid propellant, such as chlorofluorocarbon or fluorocarbon. Alternatively, the dry powder collectin composition may be dissolved or suspended in a solvent, such as water, ethanol, or saline, and administered by nebulization.

Prior to use, dry powders are generally stored under ambient conditions, specifically at temperatures at or below about 25° C., and relative humidity ranging from about 30 to 60%. If a low relative humidity condition (e.g., less than about 30%) is desired, it may be achieved by the incorporation of a desiccating agent in the secondary packaging of the dosage form.

In another embodiment, the dry powder collectin composition may also be formulated in solid dosage forms such as tablets and capsules for oral administration. For example, a capsule may be designed to release the active portion of the formulation at the point in the gastrointestinal tract when bioavailability is maximized and pre-systemic degradation is minimized. Additional agents can be included to facilitate absorption of the collectin. Diluents, flavorings, low melting point waxes, vegetable oils, lubricants, suspending agents, tablet disintegrating agents, and binders may also be employed. The dry powder collectin composition may also be formulated in sustained- or controlled-delivery forms. Techniques for formulating a variety of other sustained- or controlled-delivery means, such as liposome carriers, bio-erodible microparticles or porous beads and depot injections, are also known to those skilled in the art.

In yet another embodiment, the dry powder collectin composition may be formulated for parenteral administration. Parenteral administration is commonly understood as administration by other than gastro-intestinal, pulmonary, and topical routes. Suitable parenteral routes for administering the dry powder collectin composition of the present invention include intravenous, intramuscular, subcutaneous, intraperitoneal, intraarterial, and buccal routes. Intravenous, intraperitoneal, intramuscular, and subcutaneous routes of administration of the dry powder collectin composition are more suitable for the dry powder collectin composition of the present invention.

Administration via certain parenteral routes may involve introducing the formulations of the present invention into the body of a patient through a needle or a catheter, propelled by a sterile syringe or some other mechanical device such as a continuous infusion system. The formulations provided by the present invention may be administered using a syringe, injector, pump, or any other device recognized in the art for parenteral administration. The formulations may also be administered for absorption through the mucus membranes, such as in buccal administration.

In still another embodiment, the dry powder collectin composition can also be administered topically, directly to cavities and sites of microbial infection on the surface for treatment and/or prevention of such infections.

While the dry powder collectin compositions of the present invention can be administered as the sole active pharmaceutical agent, they can also be used in combination with one or more other suitable therapeutic agents, such as antifungal agents, antibiotics, or antiviral agents. When administered as a combination, the therapeutic agents can be formulated as separate compositions that are given at the same time or different times, or the therapeutic agents can be given as a single composition.

The effective amount of the therapeutic agents in the dry powder collectin composition to be employed therapeutically depends on a number of factors, among which are included, without limitation, the patient's sex, weight and age, the underlying causes of the condition or disease to be treated, the route of administration and bioavailability, the persistence of the administered therapeutic agents in the body, the formulation, and the potency of the active component.

The frequency of dosing also depends on those factors as described above, including the pharmacokinetic parameters of the therapeutic agents in the formulation being used. Typically, a clinician will administer the composition until a dosage is reached that achieves the desired clinical result. The dry powder collectin composition may therefore be administered as a single dose, as two or more doses (which may or may not contain the same amount of the active ingredient) over time, or as a continuous infusion via an implantation device or catheter. It is within the skill of the ordinary physician to titrate the dose and infusion rate or frequency of administration of the formulation of the present invention to achieve the desired clinical result.

Therapeutic Implications

A number of clinical diseases and conditions may be treated by the dry powder collectin composition of the present invention, particularly, those associated with infections, collectin deficiency, such as MBL deficiency, and immunocomprised conditions. The dry powder composition of the present invention may particularly be suitable for treating and preventing microbial infections. As have been demonstrated, the carbohydrate recognition domains (CRD) of a collectin protein are capable of recognizing and binding these carbohydrates commonly expressed by microbes (Hans-Jurgen et al, *Protein Science*, 3:1143, 1994). For example, CL-43 binds gp160, a glycoprotein that constitutes the outer coat of human immunodeficiency virus (HIV), to inhibit its binding to CD4 receptors (Anderson et al, *Scand. J. Immunology*, 32:81, 1990). Human conglutinin-like protein is known to bind HIV-1's gp120 to block infection (Ushijima et al, *Jpn. J. Cancer Res.*, 83:458, 1992). There have been reports on SP-A and SP-D as well that these proteins block microbial infection by binding to the microbes (Zimmerman et al, *J. Clin. Invest.*, 89:143, 1992; McNeely et al, *J. Infect. Dis.*, 91, 1993; Kuan et al, *J. Clin. Invest.* 90:97, 1992).

The infectious microorganisms which are treatment and prevention targets for the present invention are, for example, viruses, bacteria, fungi, parasites. Suitable virus targets include the viruses with outer coats, such as influenza virus, human immunodeficiency virus, herpes virus, SARS corona virus and rhinovirus. Suitable bacteria targets include those with glycosylation patterns recognizable by collecting, including *Staphylococcus aureus*, *Hemophilus influenzae* and *S. pyogens*. Suitable fungal targets include *Candida albicans*.

Treatment of diseases and disorders herein is intended to also include the prophylactic administration of a composition of the invention, a pharmaceutical salt thereof, or a pharmaceutical formulation of either to a subject (i.e., an animal, a mammal, or a human) believed to be in need of preventative treatment, such as, for example, infection and the like.

EXAMPLES

The following examples serve to provide further appreciation of the invention but are not meant in any way to restrict the effective scope of the invention. Unless otherwise mentioned, the percentage used in the examples below refers to weight-to-volume ratios.

Example I

Characterization of MBL Powder and Establishment of the Method for its Analysis

To formulate recombinant mannose-binding protein (MBL) into a form suitable for inhalation, treating external wounds or into a powdered form which in turn can be formulated into tablets, the following conditions are met: the quaternary structural characteristics of MBL oligomer complexes are maintained throughout the spray-drying process; and the powder produced exhibits substantial complement activation in the presence of glycosylated MBL-binding proteins and serine proteases upon dissolution. In addition, the spray-dried MBL powder is aerosolizable for effective pulmonary administration.

a. Preparation of a Spray-Dried MBL Powder Composition:

The MBL solution used for spray-drying was prepared as follows: 5 µg/mL recombinant MBL (Dobeel, Korea), 150 mM NaCl, 10 mM $CaCl_2$, 1 mg/mL casein, and 0.4% (w/v) sucrose. The MBL solution was spray dried using a laboratory spray-dryer, LaPlant SD-05 (UK), to produce aerorsolizable white powder. The MBL solution was fed into a nozzle (0.5 mm in diameter) at the rate of 3.5 mL/min by a peristaltic pump, with the spraying rate at 1,600 L/hr. The hot air flow through a drying duct was at 1,150 L/min, and the feed or inlet temperature was kept at 100° C., while the discharge or outlet temperature was at 69° C. The spray-dried MBL powder as characterized by the methods described below.

b. Particle Characterization:

The particle sizes and distribution of the spray-dried MBL powder composition were analyzed using a laser zeta potentiometer (ELS-8000, Otsuka Electronics, Japan). As shown in FIG. 1, the aerorsolizable MBL powder composition had particle sizes ranging between 2.18 and 3.18 µm, the average size or the mass median diameter being 2.57±0.24 µm, which is within the particle sizes (5 µm or below) typically required for effective delivery of the composition to respiratory ducts and lungs.

c. Western Blot Analysis

Figure 2:
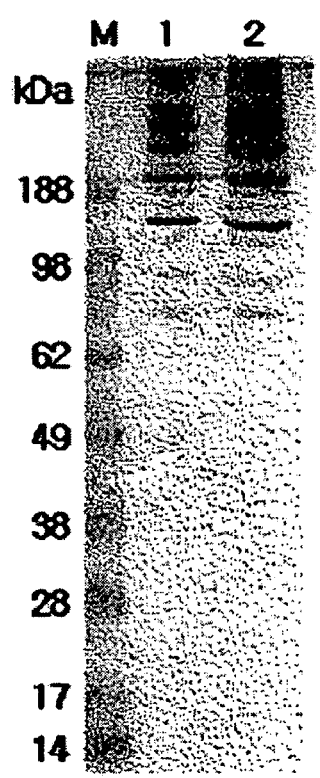
FIG. 2 shows the Western blot analysis of a spray-dried MBL powder composition (lane 2) in comparison with the MBL control solution (lane 1). Lane M is molecular weight markers.

Western blot was used to assess whether there were significant changes in the oligomer complexes (i.e. quandary structures) of the MBL powder composition. Western blot analysis was carried out under non-denaturing conditions to compare the aggregation pattern of the processed MBL with the original MBL in solution, from which the spray-dried MBL was produced. As shown in FIG. 2, there are no notable differences in aggregation pattern between the spray-dried and the original solution MBL, which suggests that the dried powder MBL most likely does not have significant changes in its quandary structures.

d. Functional MBL ELISA:

The biological activity of MBL was assessed quantitatively using a functional enzyme-linked immunosorbent assay (ELISA), which measures the ability of MBL/MASP complexes to initiate C4 complement cleavage when MBL is bound to mannan. Briefly, an immunoassay microplate (MAXISORP™ Immunoplate, Nunc, Denmark) was coated with hepatitis B pre-S antigen at 500 ng/well. An MBL sample solution was prepared by dissolved a spray-dried powder in water or buffer. The MBL sample and control solutions were added to individual wells on the microplate plate at 200 ng, 100 ng, 50 ng, 25 ng, 12.5 ng, 6.25 ng or 3.125 ng per well. The solutions in microwells were incubated for 2 hours at room temperature to allow binding. The reaction mixture was removed and the plates were washed 6 times with wash buffer. MBL-free serum solution was prepared from a MBL-free serum stock solution (Dobeel, Korea) via a 100 fold dilution with a dilution buffer. The diluted MBL-free serum solution (100 µL) was then added to each well to provide MBL-associated serine proteases (MASPs). After the plate was washed 6 times with wash buffer, a C4 (500 ng) in solution was added to each well on the plates, followed by a 2-hour incubation. Anti-C4 horseradish peroxidase (HRP) conjugate after diluted 1,500 fold from a stock solution (Biogenesis, UK) was added, followed by an 1-hour incubation. A solution of o-phenylenediamine ("OPD") (150 µL per well) was added and the colorimetric reaction was allowed to proceed for 20 minutes to detect C4b deposits. The reaction was stopped by adding 50 µL of 3M HCl, the absorbance was measured at 492 nm with an ELISA reader.

Figure 3:
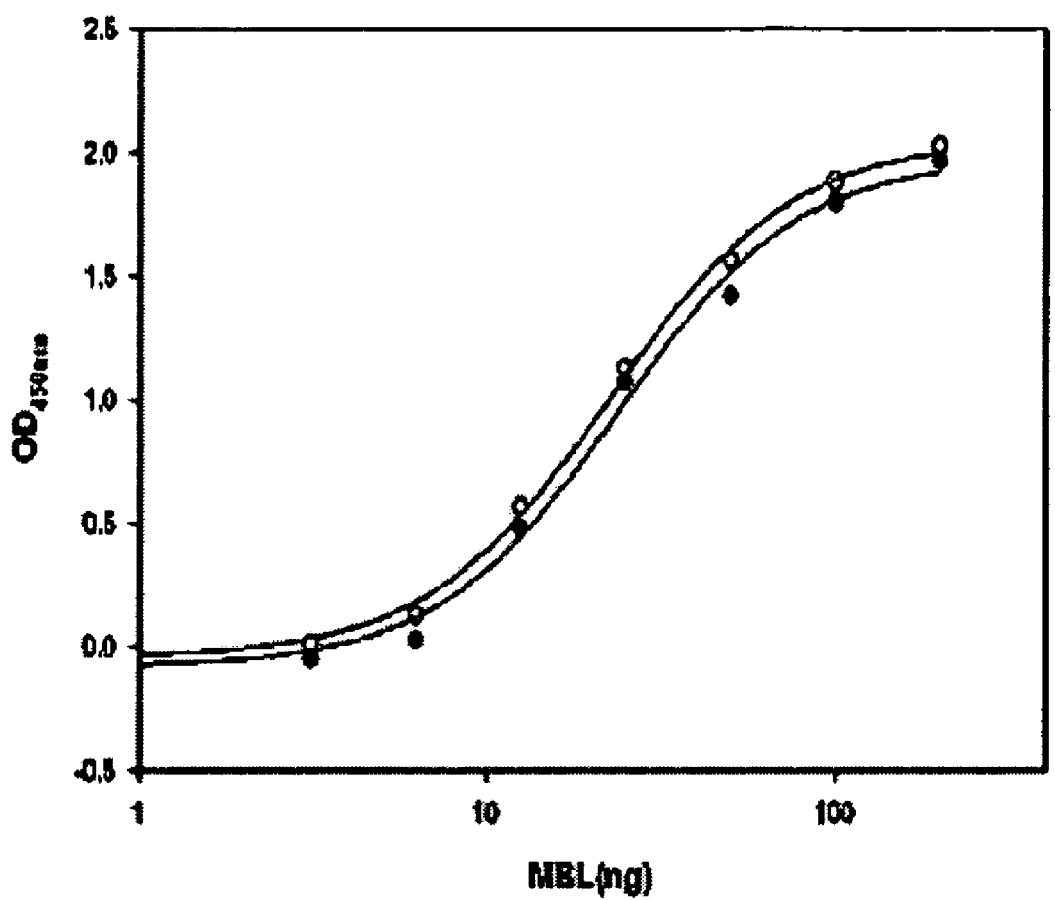
FIG. 3 compares the C4 activation level of a spray-dried MBL powder composition (open circles) versus the MBL control solution (filled circles), as measured with a functional MBL ELISA as described herein in detail in Example 1 d.
Figure 4A:
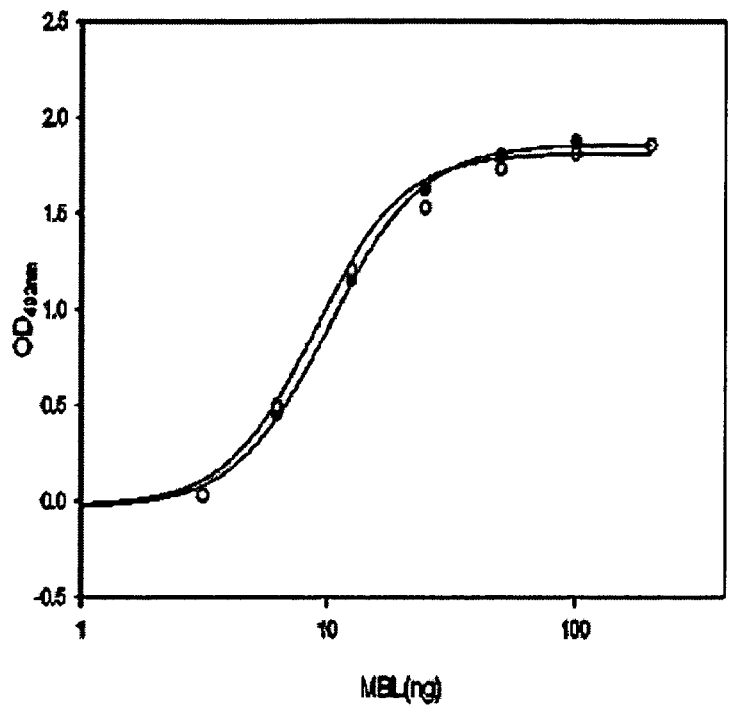
(FIG. 4A), 100° C./68° C.
Figure 4B:
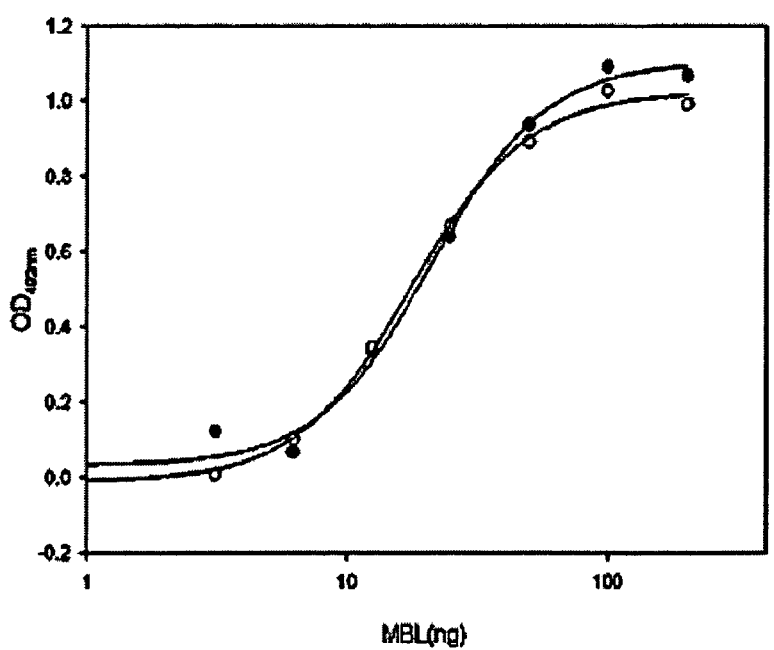
(FIG. 4B), 115° C. /78° C.
Figure 4C:
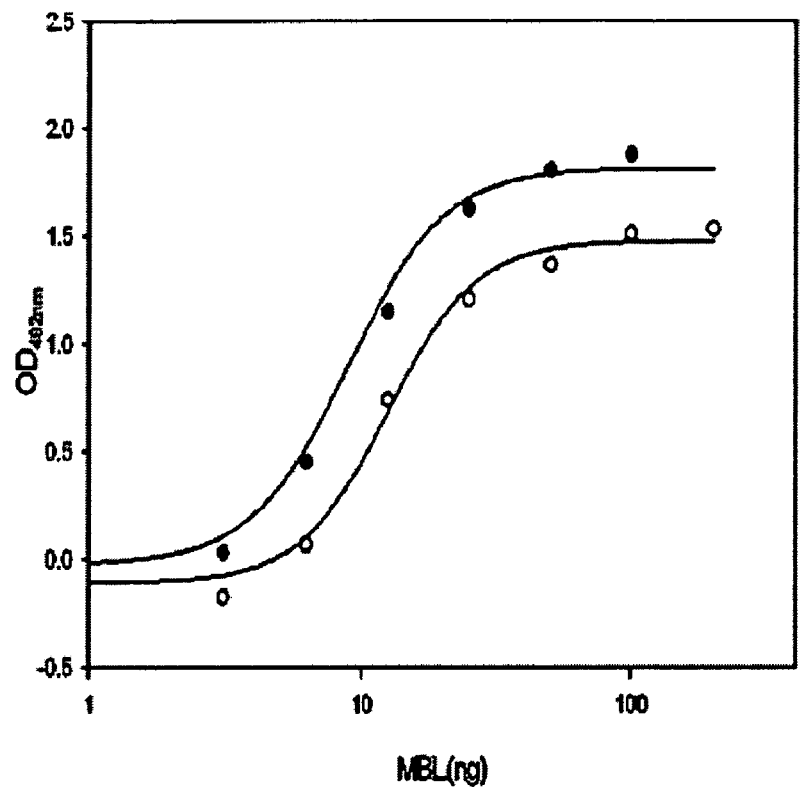
(FIG. 4C), 130° C. /87° C.
Figure 4D:
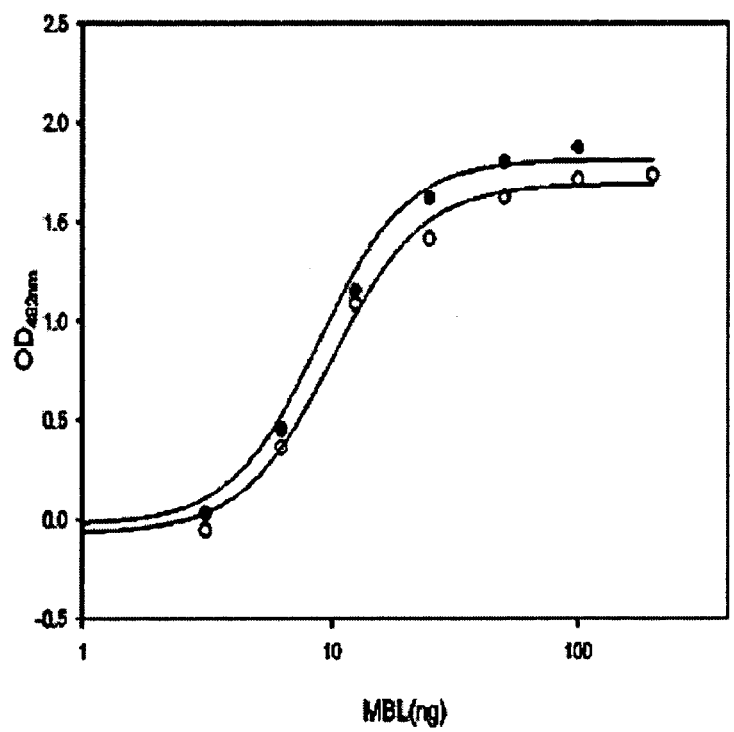
(FIG. 4D), or 150° C./100° C.
Figure 4E:
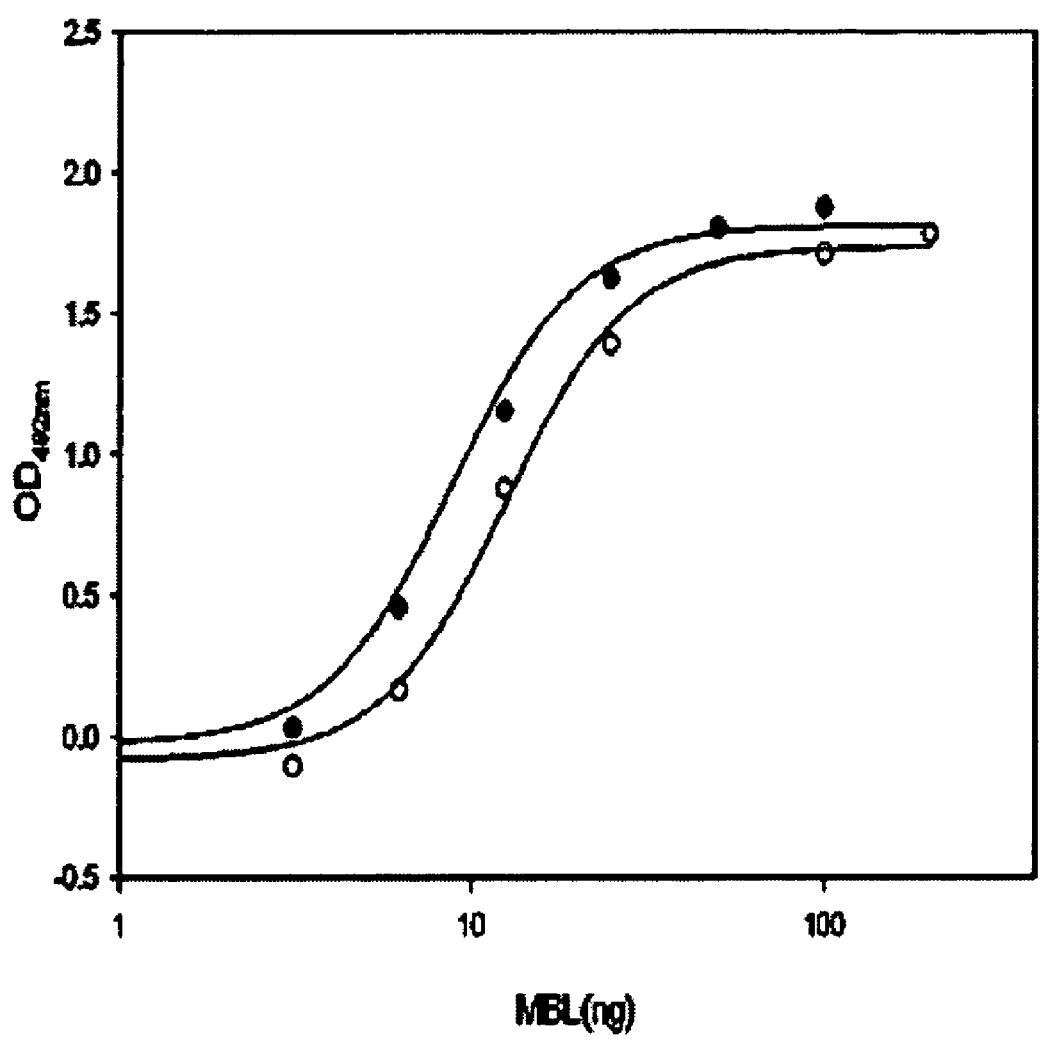
(FIG. 4E) versus the MBL control solution (filled circles), as measured with a functional MBL ELISA as described herein in detail in Example 1 d.

The biological activity of the spray-dried MBL powder composition prepared above is shown in FIG. 3 together with the MBL control, the MBL solution, from which the spray-dried MBL powder was produced. As shown in FIG. 3, both the MBL control and the spray-dried MBL exhibit similar levels of biological activities.

In summary, the present invention has provided the spray-dried MBL powder composition which has 1) an inhalable particle size, 2) displays no significant structural changes as estimated by Western blot analysis, and 3) still retains its complement-activating ability.

Example II

Effect of Air Temperatures on the Biological Activity of Spray-Dried MBL Powder Composition Most proteins are prone to denaturation by heat, and thus lose their biological activities. Since spray-dryers convert liquid samples into powders using hot air flow, the air temperature was optimized by examining the differences in complement activation of MBL powders produced under a series of different temperature conditions in the presence of glycosylated, MBL-binding proteins and serine proteases.

The MBL solution used for spray-drying had the following composition: 5 µg/mL recombinant MBL, 150 mM NaCl, 10 mM $CaCl_2$, 250 µg/mL casein, and 2% (w/v) sucrose. The feed/discharge temperatures, that is, inlet/outlet temperatures, for spray-drying were set at 80° C./58° C., 100° C./68° C., 115° C./78° C., 130° C./87° C., and 150° C./100° C., respectively. Each dry powder MBL composition produced under its own temperature condition was compared with the MBL control for its ability to activate C4 in the complement system by using the functional MBL ELISA as described above. As shown FIGS. 4A to 4E, the spray-dried powder MBL compositions at temperature settings of 80° C./58° C. and 100° C./68° C. have similar activities to the MBL controls, whereas the spray-dried powder MBL compositions produced at higher temperature settings suffer from reduction in their activities as the temperature goes up.

Example III

Effects of Carbohydrate Excipients on the Spray-Dried MBL Powder Compositions

When spray-drying proteins into powder formulations using hot air, it is common practices to add various kinds of pharmaceutically acceptable excipients in the compositions to further enhance physical and biological stability. In this example, the effects of four different carbohydrates as stabilizers on the physical characteristics and biological stability of the spray-dried MBL powder compositions were evaluated with functional MBL ELISA for the levels of C4 activation, with a laser zeta potentiometer for particle sizes and particle size distributions, and by a scanning electron microscope for particle shapes.

Figure 5A:
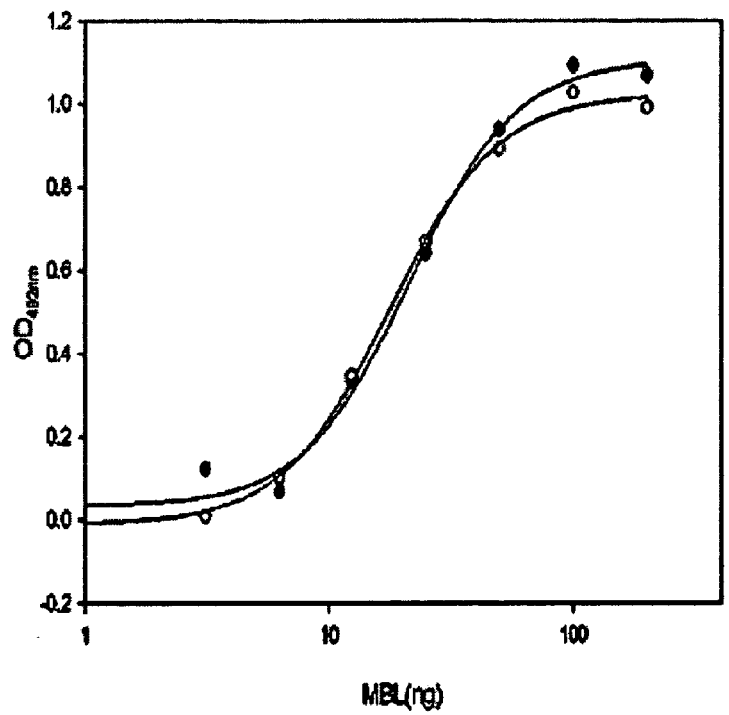
FIGS. 5 A-D compare the C4 activation levels of spray-dried MBL powder compositions (open circles) produced in the presence of four different carbohydrates: sucrose (FIG. 5A), lactose (FIG. 5B), trehalose (FIG. 5C), or pluran (FIG. 5D) versus the correspondent MBL control solutions with the same carbohydrate contents (filled circles), as measured using a functional MBL ELISA as described herein in detail in Example 1 d.
Figure 5B:
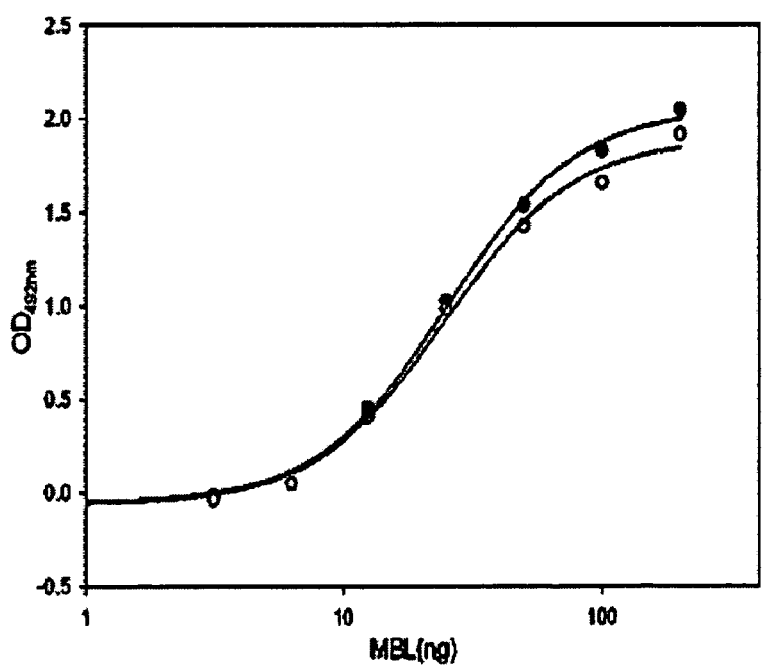
Figure 5C:
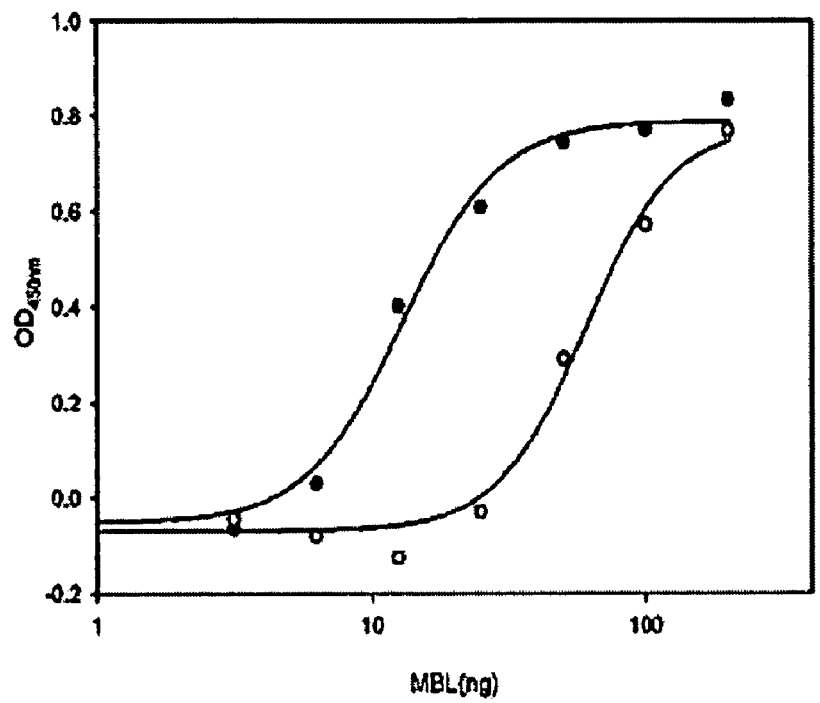
Figure 5D:
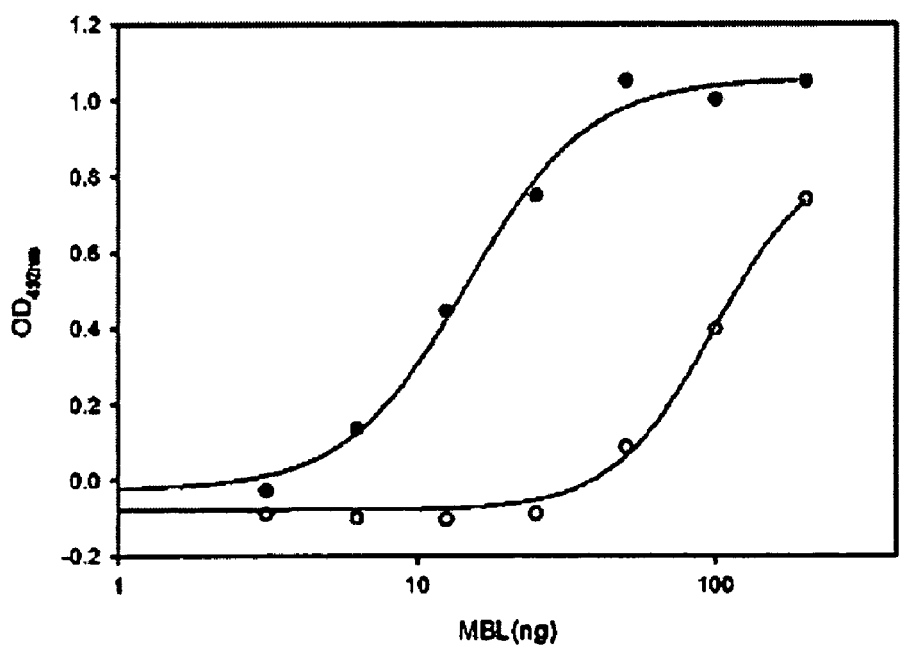

Four spray-dried MBL powder compositions were prepared from their correspondent MBL solutions, which each contains 5 µg/mL recombinant MBL, 150 mM NaCl, 10 mM $CaCl_2$, 250 µg/mL casein, and a carbohydrate: 0.4% sucrose, 0.5% lactose, 0.4% trehalose, or 0.4% pluran. The effects on biological activities were shown in FIGS. 5A to 5D, by comparing the activities of the spray-dried MBL powder compositions with their correspondent MBL control solutions for their abilities to activate C4 in the complement system using the functional MBL ELISA as described above. The spray-dried MBL powder compositions which contain 0.4% sucrose (FIG. 5A) or 0.5% lactose (FIG. 5B) have nearly the same biological activities compared to the MBL controls. However, the compositions containing 0.4% trehalose (FIG. 5C) and 0.4% pluran (FIG. 5D) suffer large losses in activity. These data establish sucrose and lactose as effective stabilizing excipients for the spray-drying MBL powder compositions.

Figure 6:
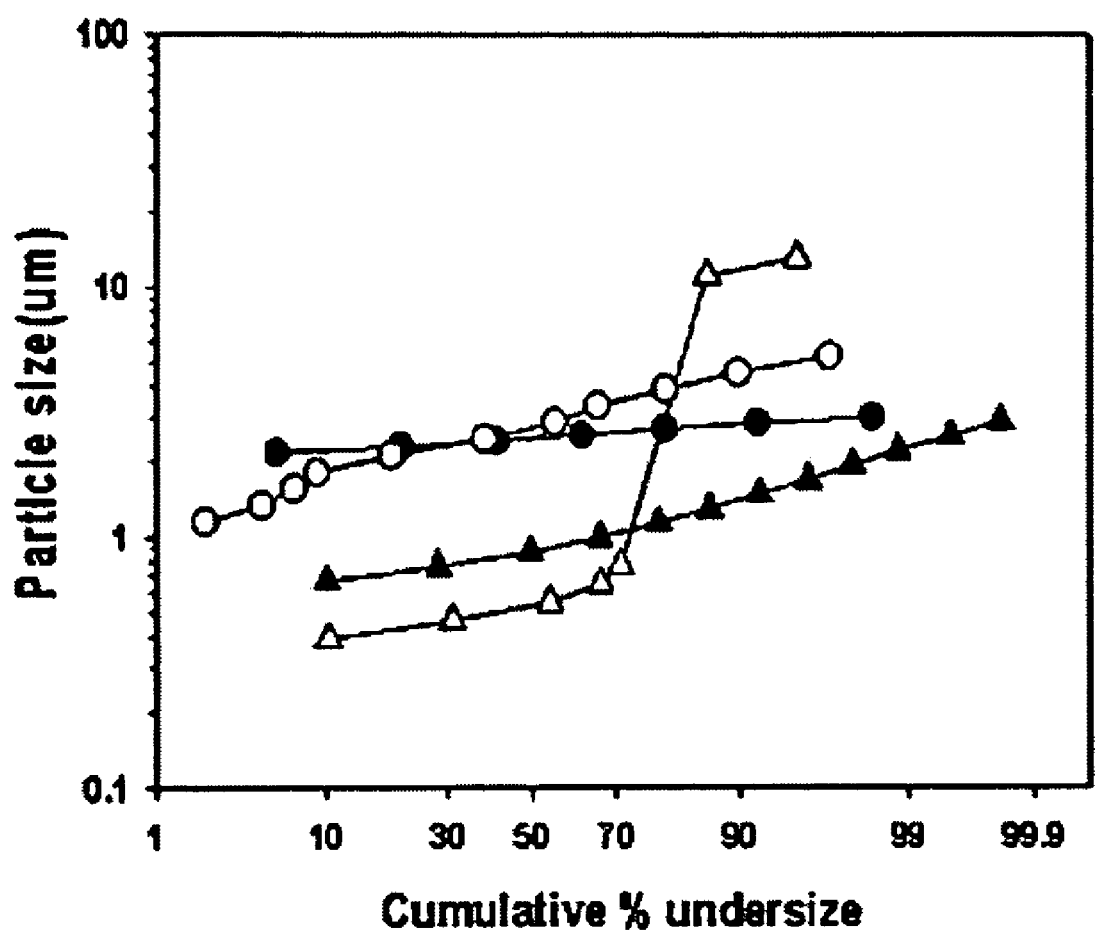
FIG. 6 shows the particle size distributions of spray-dried MBL compositions produced in the presence of four different carbohydrates: sucrose (filled circles), lactose (open circles), trehalose (filled triangles), or pluran (open triangles).
Figure 7A:
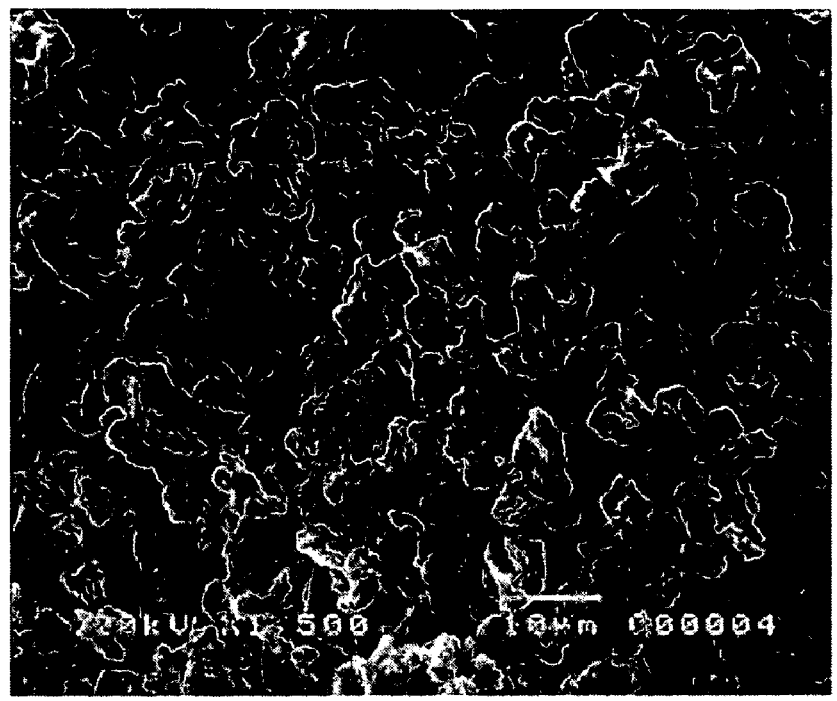
FIG. 7 show the scanning electron microscope images of spray-dried MBL composition produced in the presence of sucrose (FIG. 7A), lactose (FIG. 7B), trehalose (FIG. 7C), or pluran (FIG. 7D).
Figure 7B:
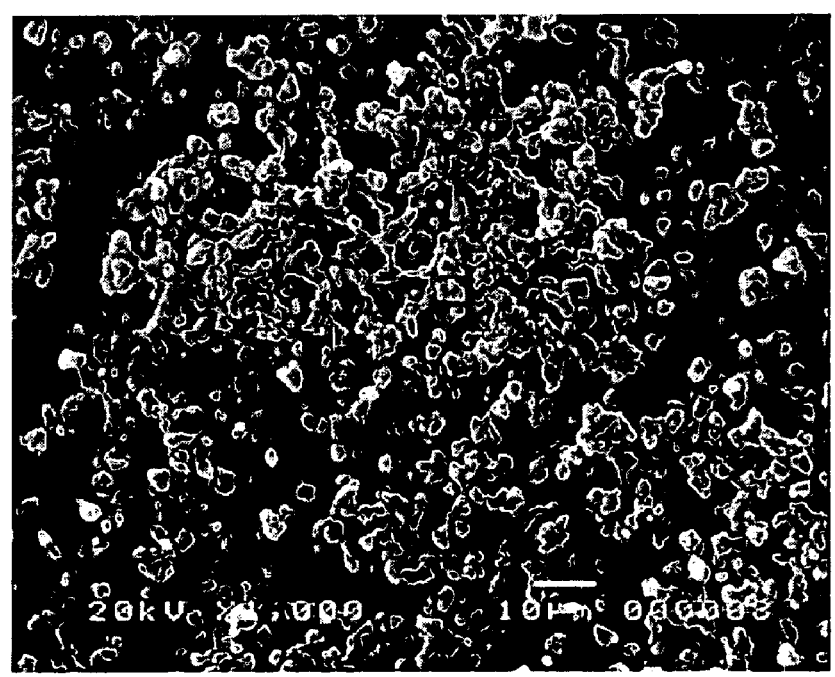
Figure 7C:
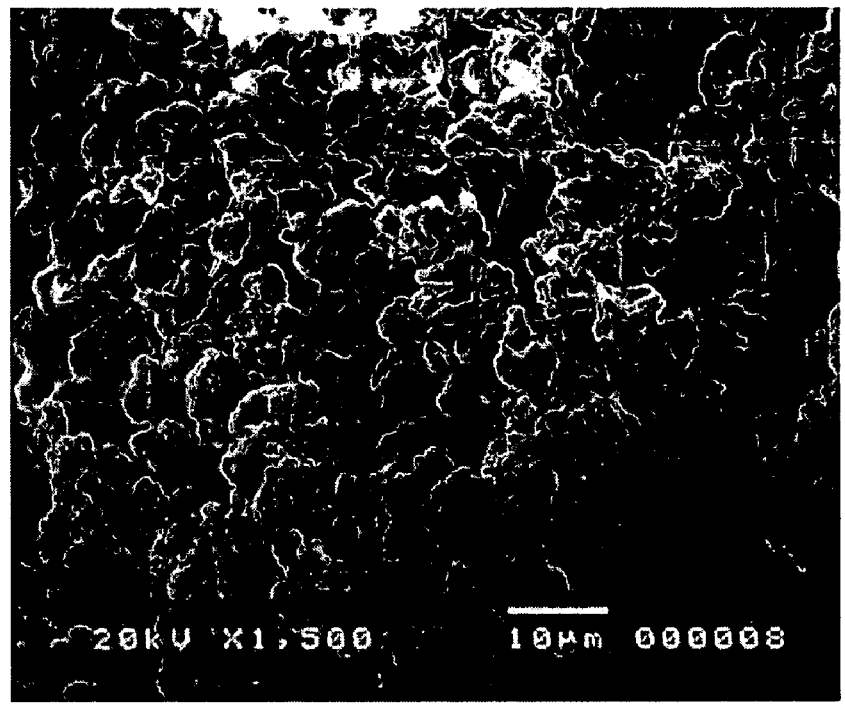
Figure 7D:
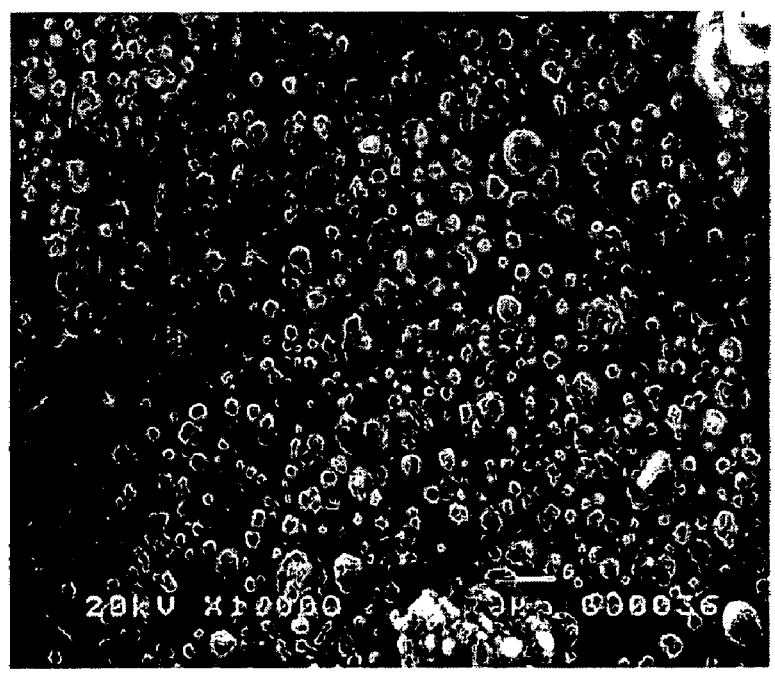
Figure 8A:
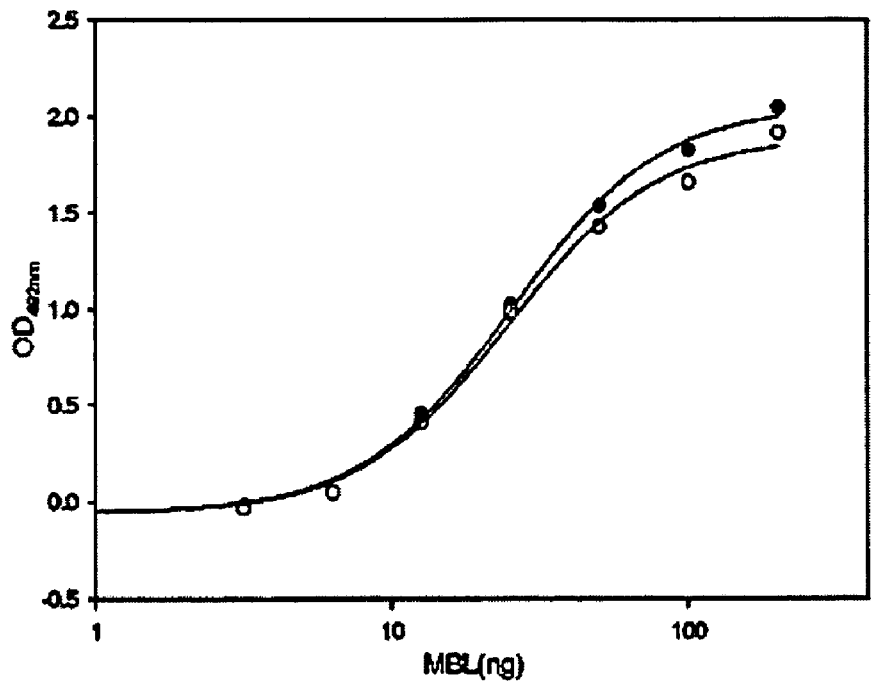
FIGS. 8 A-D compare the C4 activation levels of spray-dried MBL powder compositions (open circles) produced at four different lactose concentrations: 0.5% (FIG. 8A), 1% (FIG. 8B), 2% (FIG. 8C), or 4% (FIG. 8D) versus the correspondent MBL control solution with the same lactose concentrations (filled circles).
Figure 8B:
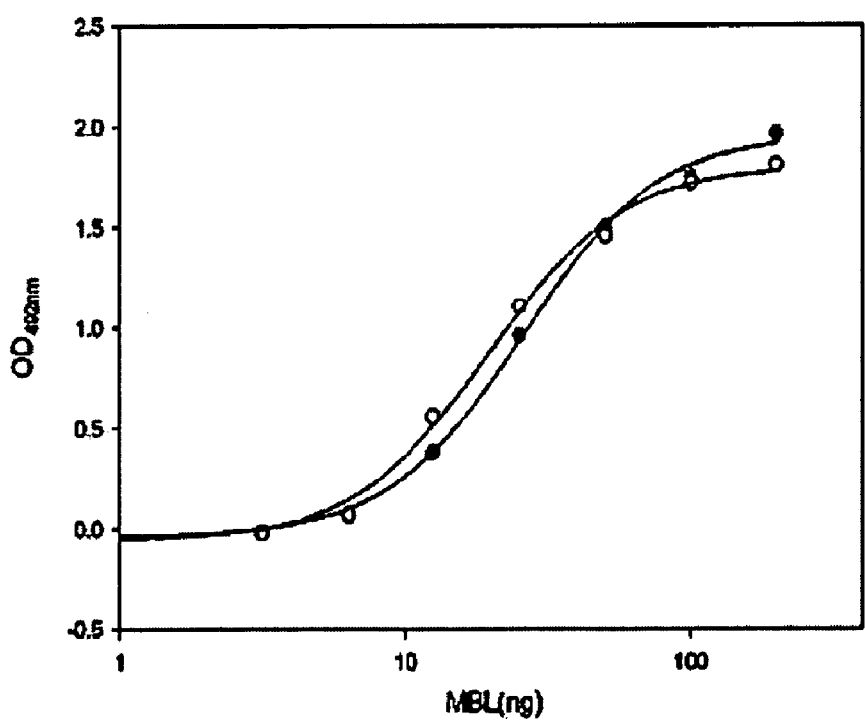
Figure 8C:
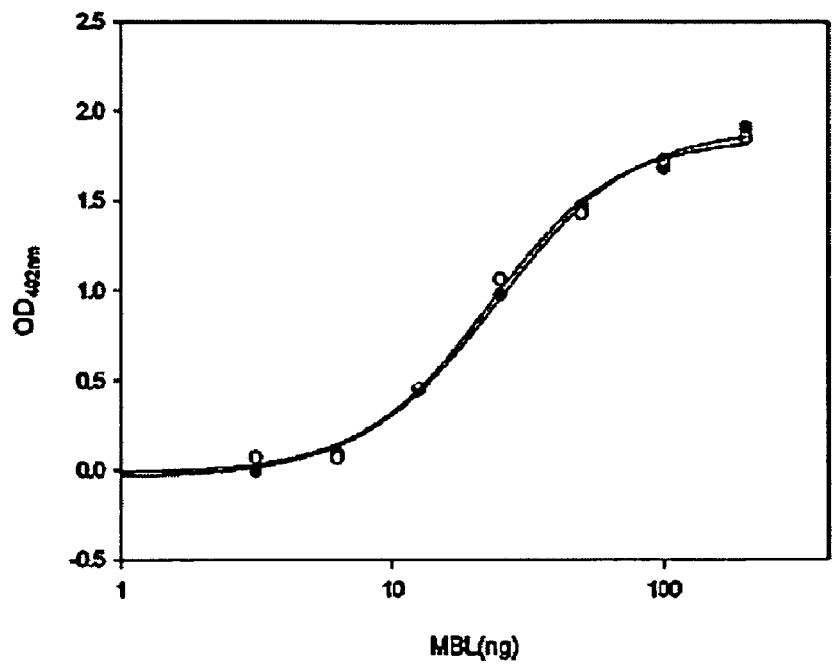
Figure 8D:
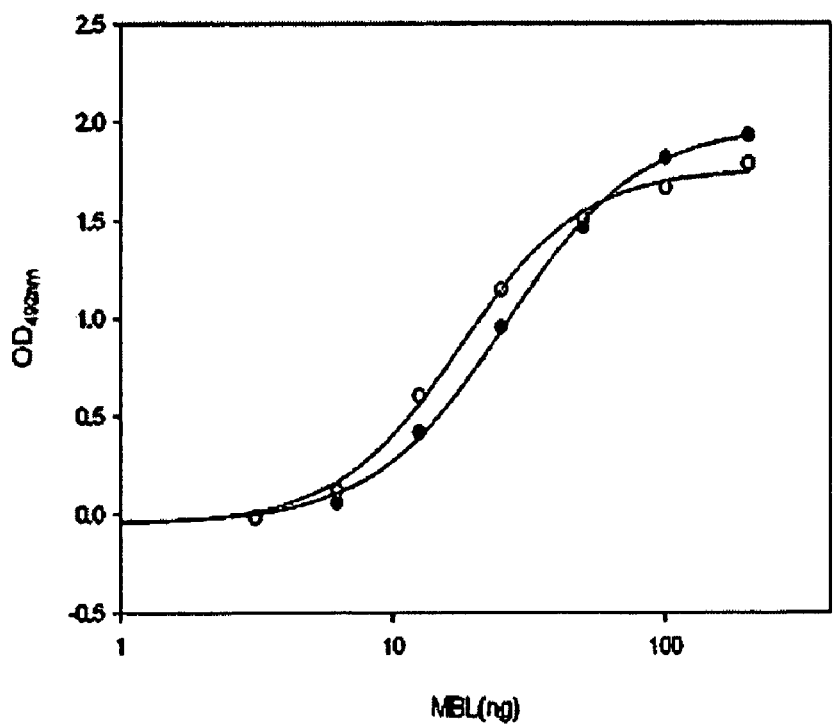
Figure 9A:
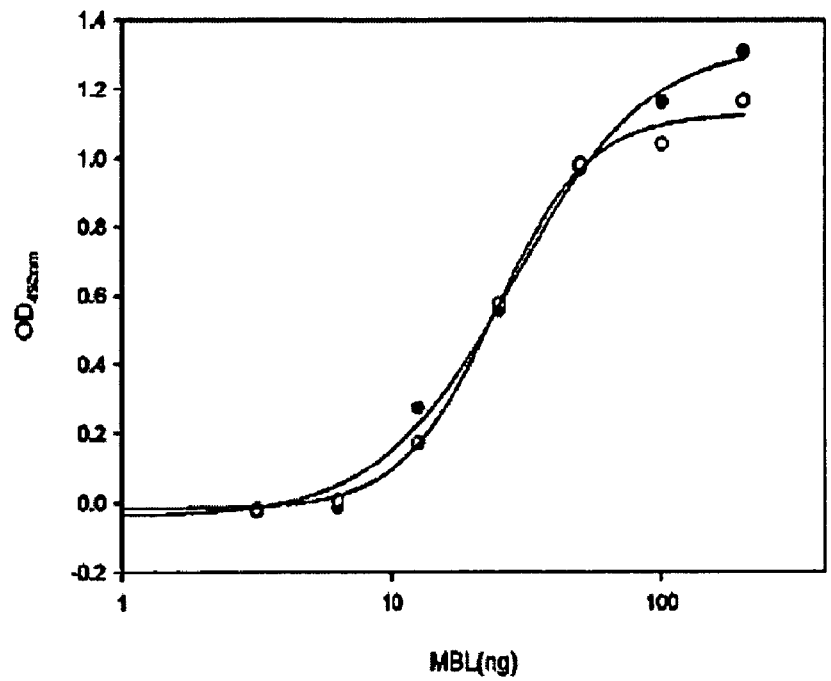
FIGS. 9 A-E compare the C4 activation levels of spray-dried MBL powder compositions (open circles) produced at five different sucrose concentrations: 0.5% (FIG. 9A), 1% (FIG. 9B), 2% (FIG. 9C), 4% (FIG. 9D), 8% (FIG. 9E) versus the correspondent MBL control solutions with the same sucrose concentrations (filled circles).
Figure 9B:
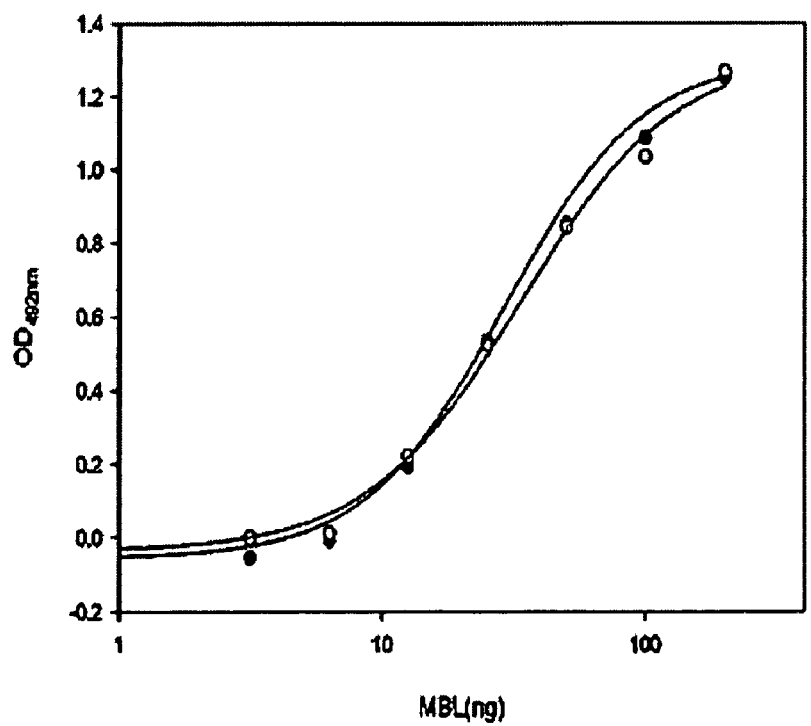
Figure 9C:
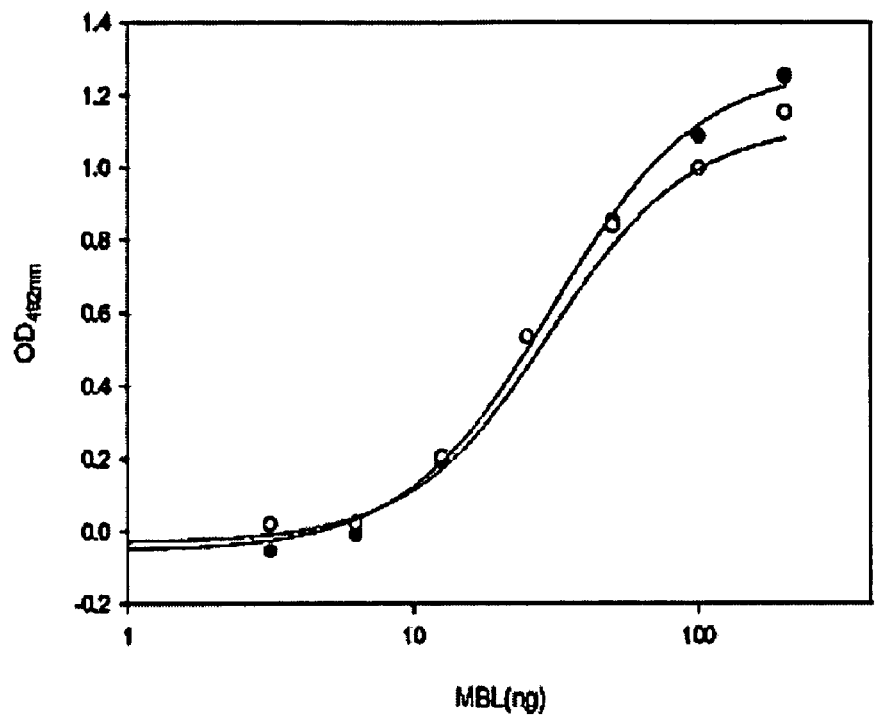
Figure 9D:
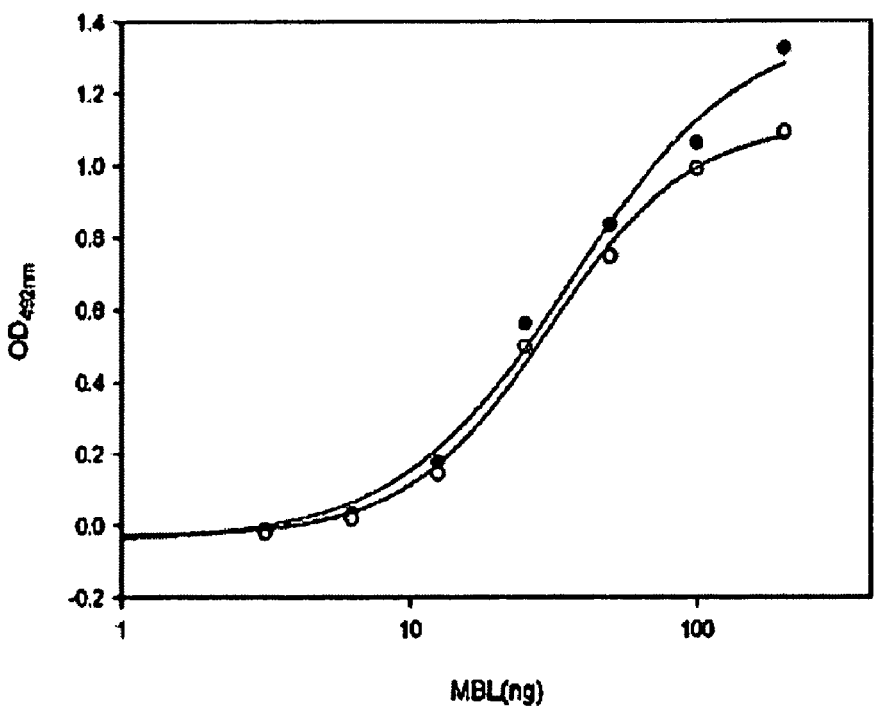
Figure 9E:
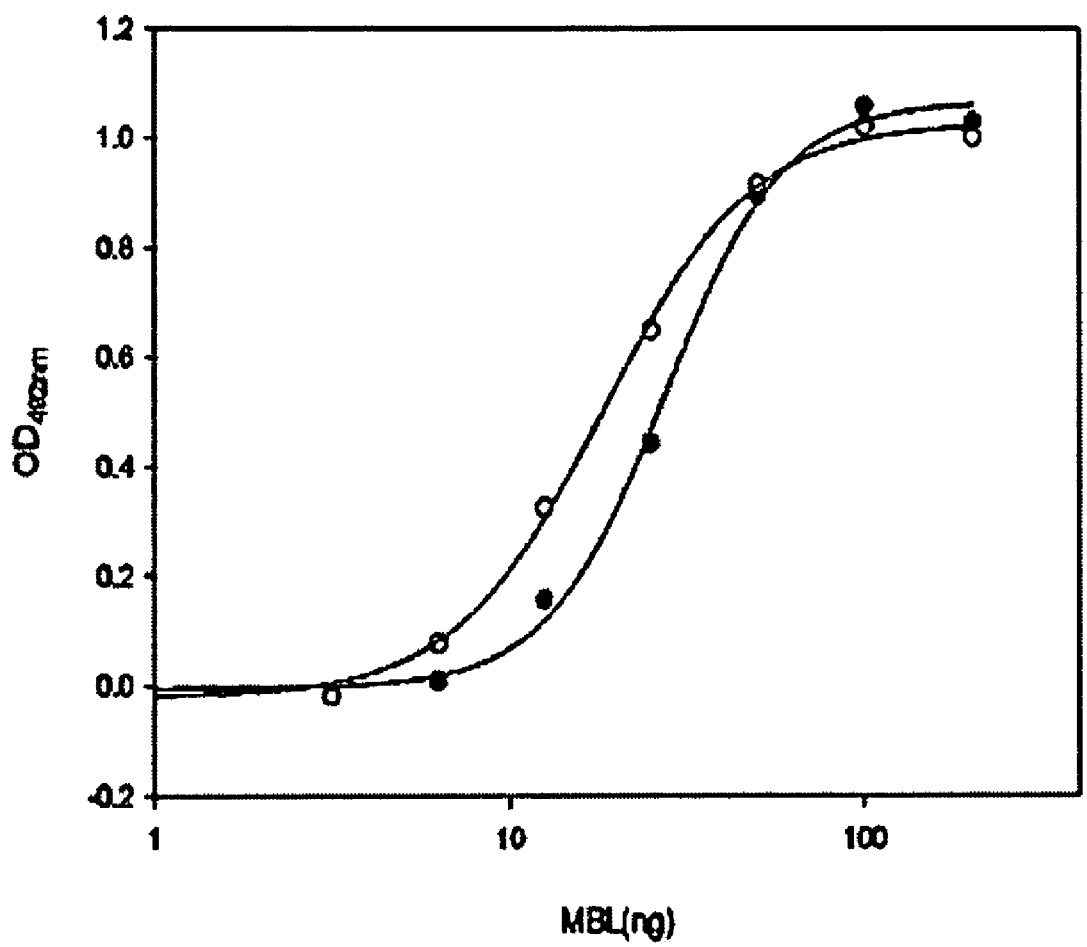

The particle size distributions of the spray-dried MBL powder compositions were probed with a laser zeta potentiometer (ELS-8000, Otsuka Electronics, Japan). As shown in FIG. 6 and Table 1, the spray-dried MBL powder compositions have particle sizes ranging from 1.04 to 4.00 µm. Addition of sucrose, lactose, or trehalose provides particles with narrow particle size distributions. Addition of pluran, however, yields a broad size distribution ranging from 0.39 to 15.43 µm. It was thus concluded that addition of sucrose, lactose or trehalose to a MBL solution was more effective than that of pluran for producing MBL powders for effective inhalation.

TABLE 1

Particle Size Distribution of the Spray-dried MBL Powder Compositions

| Carbohydrates | Minima (mm) | Maxima (µm) | Mean ± S.D. (µm) |
|---|---|---|---|
| Sucrose | 2.18 | 3.18 | 2.57 ± 0.24 |
| Lactose | 0.85 | 6.16 | 3.32 ± 1.17 |
| Trehalose | 0.23 | 3.32 | 1.04 ± 0.37 |
| Pluran | 0.39 | 15.43 | 4.00 ± 5.43 |

The particle shapes of the spray-dried MBL powder compositions were also observed with a scanning electron microscope. As shown in FIG. 7, different carbohydrate excipients used for stabilizing MBL powder compositions were observed to shape MBL powders into different forms. The results of the particle size distributions of the spray-dried MBL powder composition determined by electron microscopy are also in good agreements with these determined with a laser zeta potentiometer.

Example IV

Effects of Carbohydrate Contents on the Spray-Dried MBL Powder Compositions

When carbohydrate excipients are used to enhance the stability of spray-dried proteins, the outcome varies according to the identity and concentration of the carbohydrate. In this example, the concentration ranges suitable for spray-drying were determined. The goals of this experiment were determining the effects of carbohydrate concentrations on the C4 complement activation, particle size distribution, and particle shapes of MBL powders produced when either lactose or sucrose was added to the MBL solution. The MBL solutions used for spray-drying all contained 5 µg/mL recombinant MBL, 150 mM NaCl, 10 mM $CaCl_2$, 250 µg/mL casein, and a carbohydrate at a final concentration of 0.5%, 1%, 2%, or 4% for sucrose, or 0.5%, 1%, 2%, 4%, or 8% for lactose.

MBL powders prepared using different carbohydrate excipients were measured for their complement activation levels in the presence of MBL-binding proteins and serine proteases using functional MBL ELISA. The results for the MBL compositions containing lactose are shown in FIGS. 8A to 8D. The spray-dried MBL powder compositions show similar levels of activity to controls for the range of lactose concentrations from 0.5% to 4%; in particular, the 1% lactose formulation (FIG. 8B) shows a relatively high level of activity. The 0.5% formulation exhibited a small difference compared with controls. These results suggest that the lactose concentration in a MBL solution is preferably between 1 and 2% for obtaining an active MBL powder composition by spray-drying.

The results for the MBL compositions containing sucrose are shown in FIGS. 9A to 9E. The spray-dried MBL powder compositions have similar levels of activity to controls for the range of sucrose concentrations from 0.5% to 8%; especially, the 1% (FIG. 9B) and 2% (FIG. 9C) showed relatively high levels of activity. The 8% formulation, however, exhibited a small difference compared with controls. These results suggest that the sucrose concentration in the MBL solution is preferably between 1 and 2% for obtaining an active MBL powder composition by spray-drying.

The particle size distribution of MBL powders spray-dried at various carbohydrate concentrations were probed with a laser zeta potentiometer (ELS-8000, Otsuka Electronics, Japan). The results are summarized in FIGS. 10 and 11, and Tables 2 and 3. In Table 2 and 3, DV0.1 denotes the particle diameter at 10% accumulated volume level, whereas DV0.9 denotes the particle diameter at 90% accumulated volume level.

Figure 10:
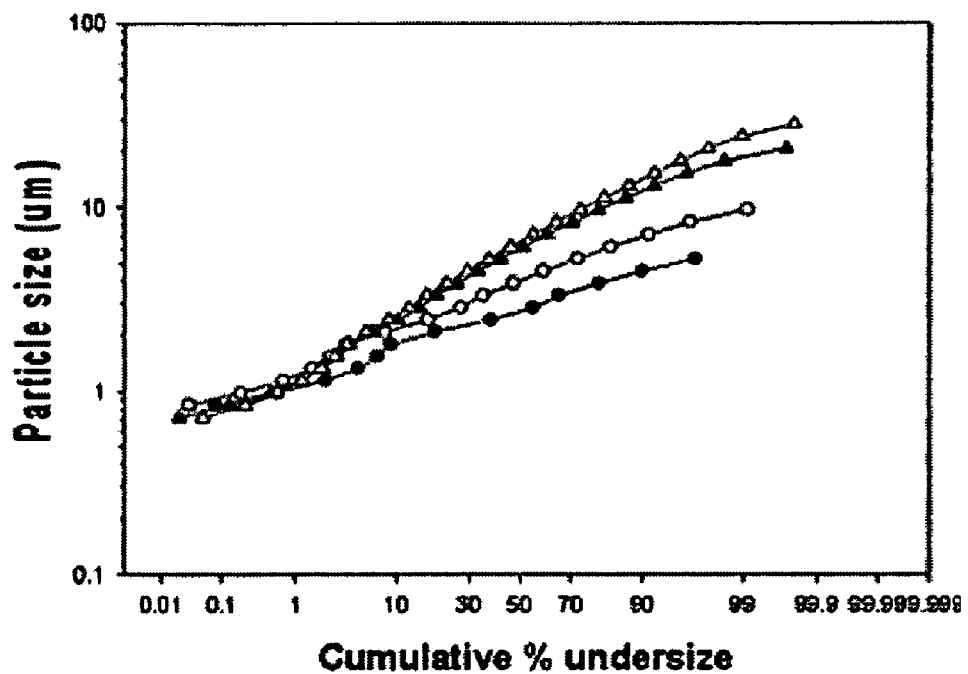
FIG. 10 shows the particle size distributions of spray-dried MBL compositions produced under four different lactose concentrations: 0.5% (filled circles), 1.0% (open circles), 2.0% (filled triangles), and 4.0% (open triangles).

As shown in FIG. 10 and Table 2, the mean particle sizes range from 3.22 to 8.32 µm for the spray-dried MBL powder compositions produced at various lactose concentrations. It is clear that an increase in the concentration of lactose, a stabilizing excipient, was accompanied by an increase in the particle size. A lactose concentration higher than 2% is corresponded to a particle size larger than 5 µm. It has been known that in order to achieve an effective delivery of spray-dried powders to respiratory tracts and lungs, the particle size should be smaller than 5 µm. The above results show that incorporating the carbohydrate excipient lactose at a concentration no greater than 2% can produce a MBL powder composition with particle sizes effective for inhalation.

TABLE 2

Particle Size Distribution of the Spray-dried MBL Powder Compositions at Various Lactose Concentrations

| Carbohydrate Concentrations | DV0.1 (µm) | DV0.9 (µm) | Mean ± S.D. (µm) |
|---|---|---|---|
| 0.5% Lactose | 2.01 | 4.90 | 3.22 ± 1.17 |
| 1.0% Lactose | 2.37 | 7.56 | 4.67 ± 2.06 |
| 2.0% Lactose | 2.64 | 13.39 | 7.36 ± 4.31 |
| 4.0% Lactose | 2.82 | 15.51 | 8.32 ± 5.35 |

Figure 11:
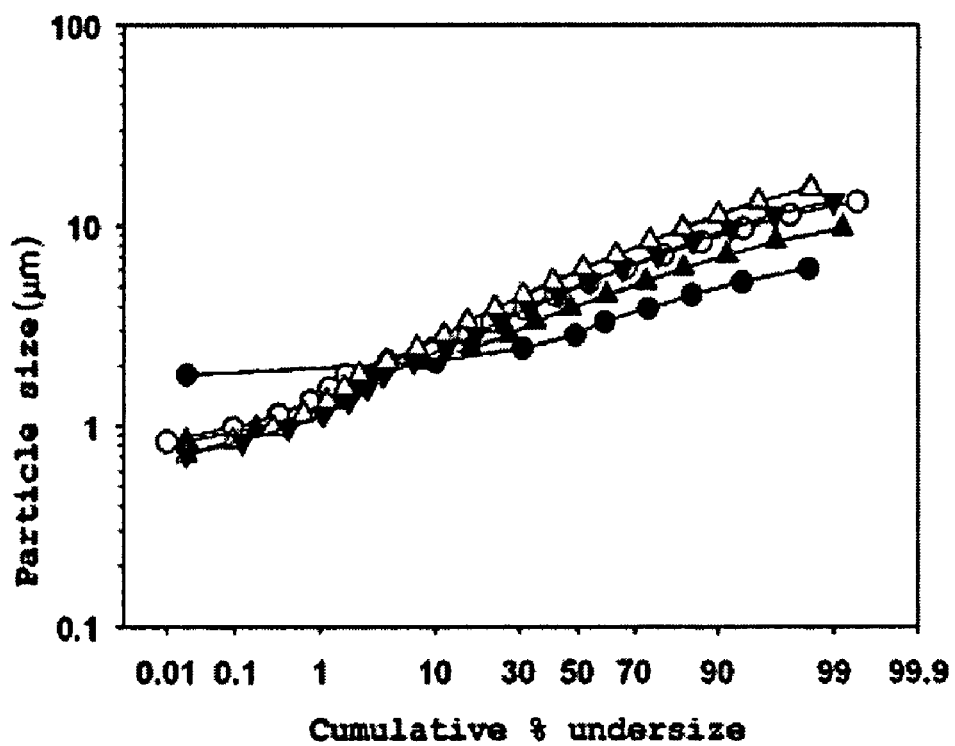
FIG. 11 shows the particle size distributions of spray-dried MBL compositions produced under five different sucrose concentrations: 0.5% (filled circles), 1.0% (open circles), 2.0% (filled triangles), 4.0% (open triangles), and 8.0% (filled inverted triangles).
Figure 12A:
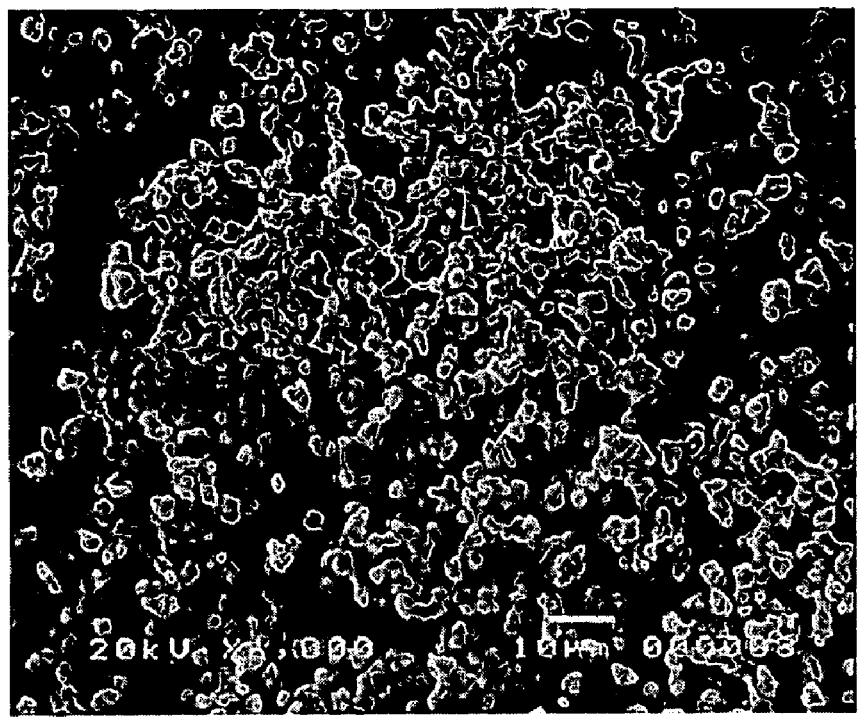
FIGS. 12 A-D show the scanning electron microscope images of the spray-dried MBL composition produced at a lactose concentration of 0.5% (FIG. 12A), 1% (FIG. 12B), 2% (FIG. 12C), or 4% (FIG. 12D).
Figure 12B:
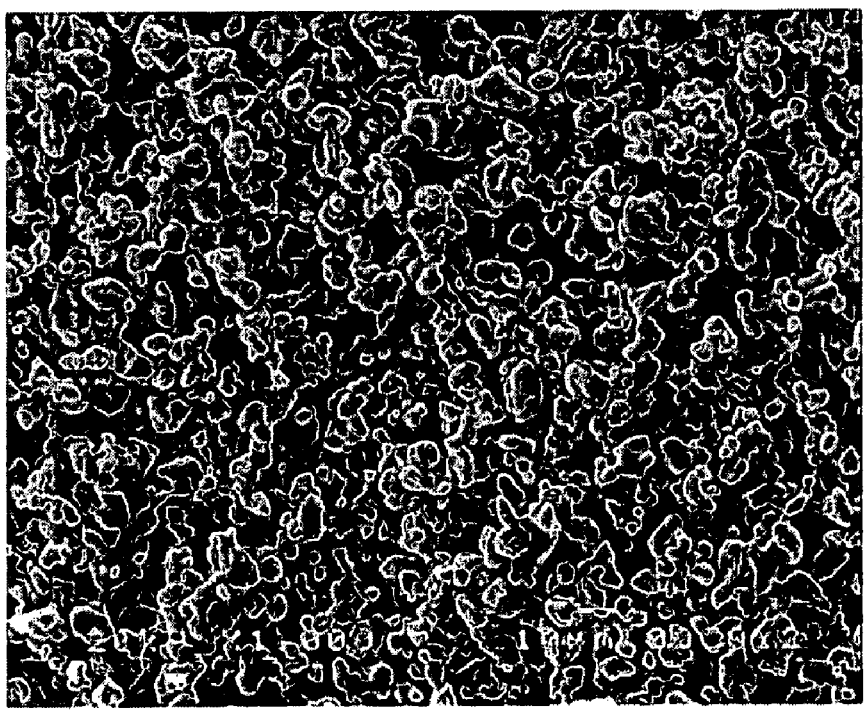
Figure 12C:
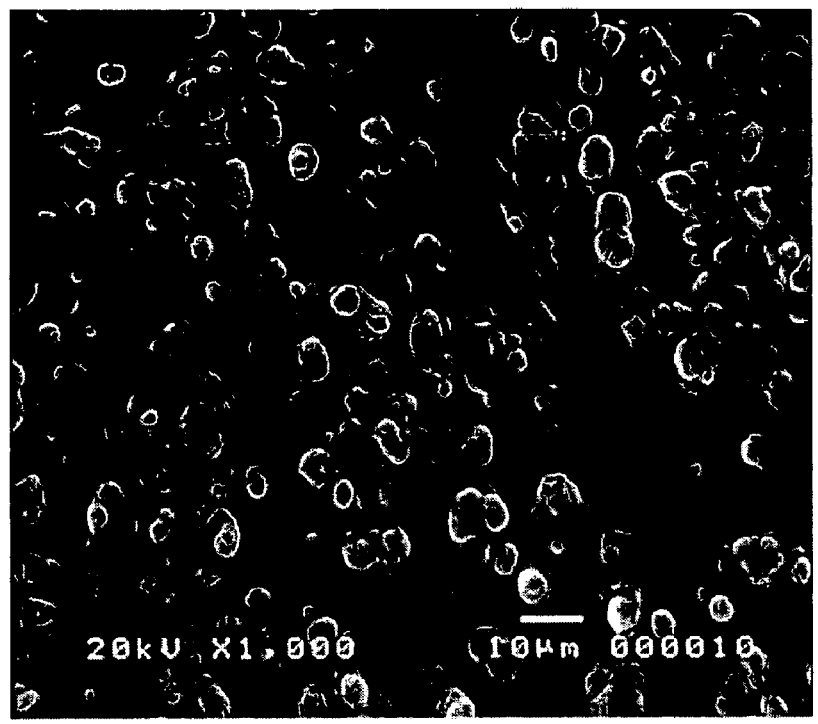
Figure 12D:
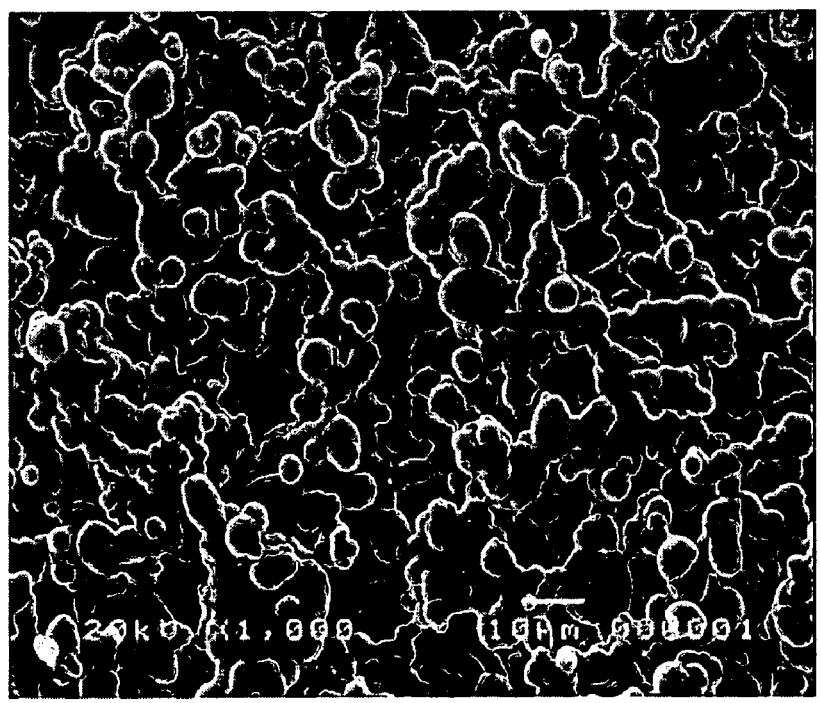
Figure 13A:
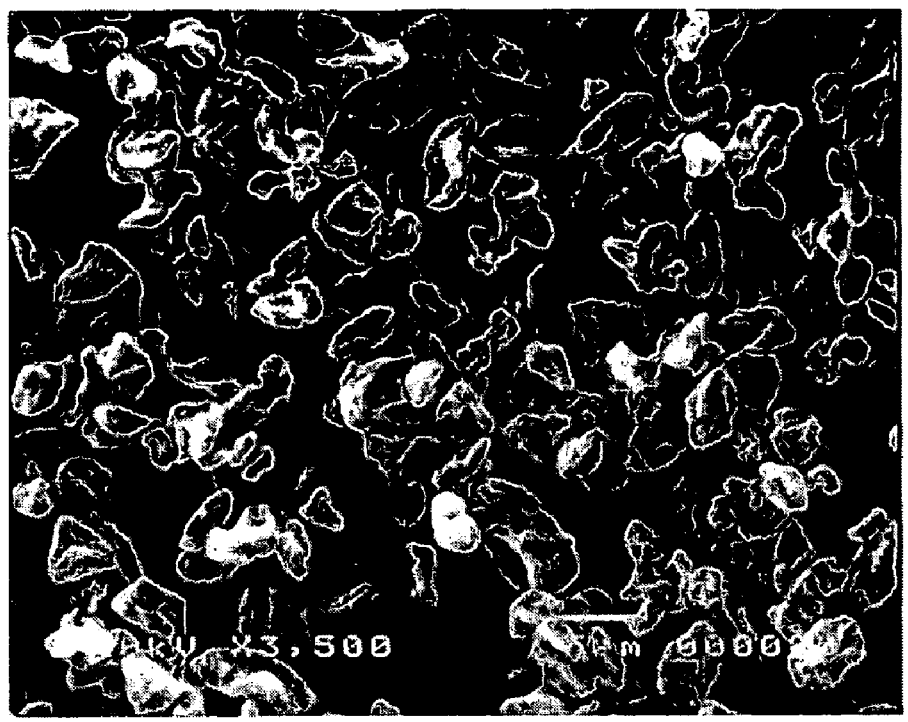
FIGS. 13 A-E show the scanning electron microscope images of the spray-dried MBL composition produced at a sucrose concentration of 0.5% (FIG. 13A), 1% (FIG. 13B), 2% (FIG. 13C), 4% (FIG. 13D), or 8% (FIG. 13E).
Figure 13B:
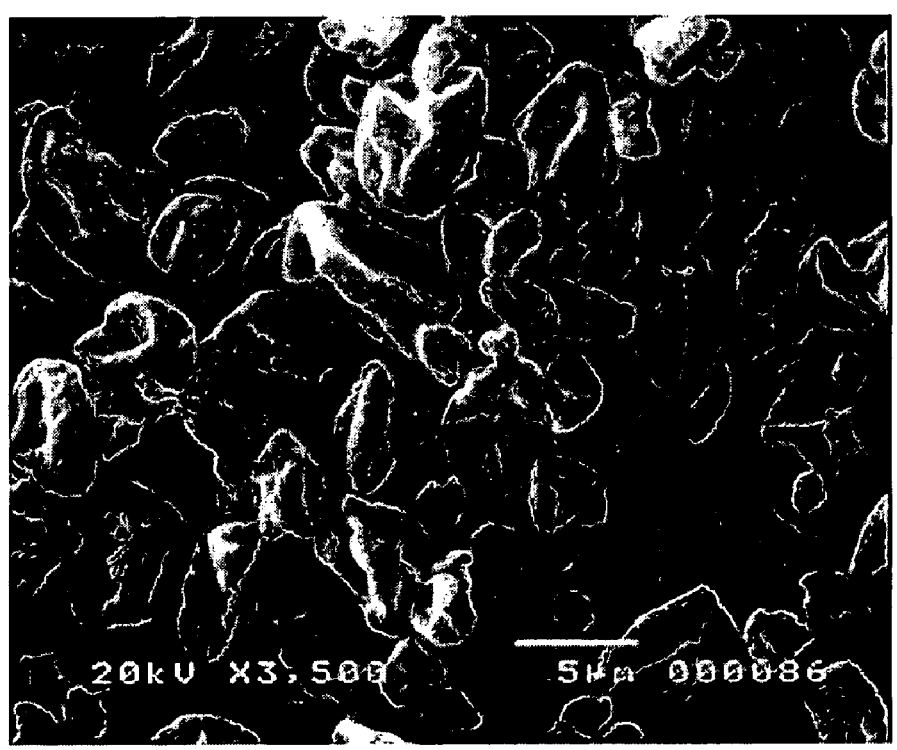
Figure 13C:
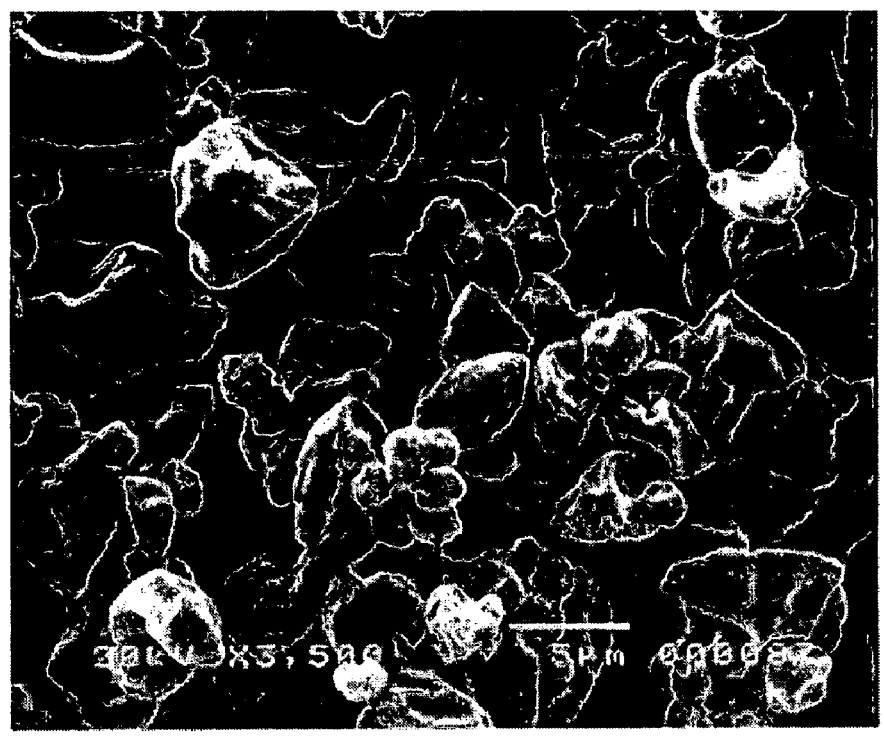
Figure 13D:
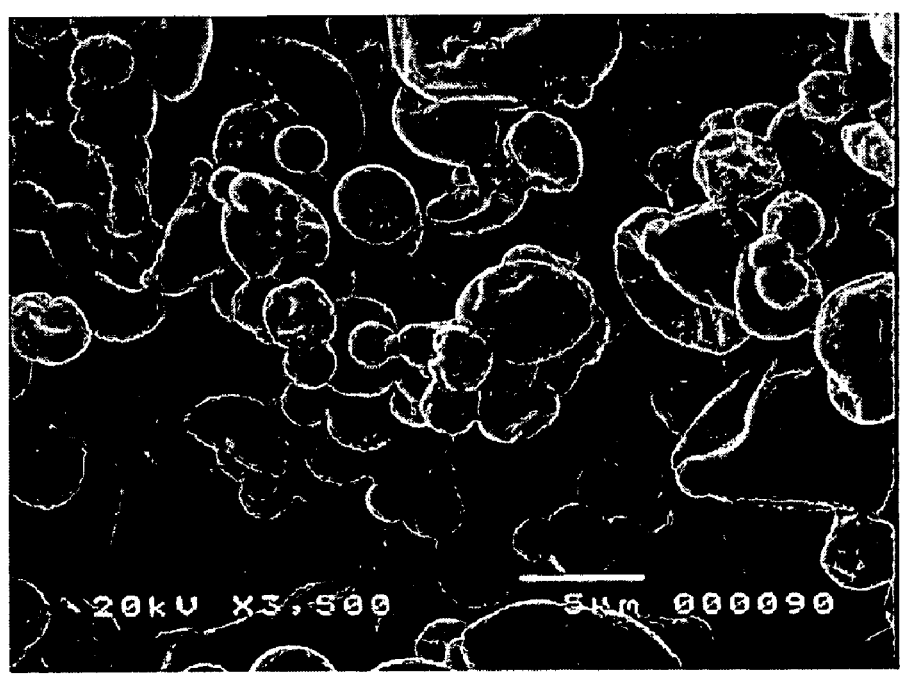
Figure 13E:

As shown in FIG. 11 and Table 3, the mean particle sizes range from 3.52 to 7.07 µm for the spray-dried MBL powder compositions produced at various sucrose concentrations. There was no clear correlation between the concentration of sucrose, a stabilizing excipient, and the particle size. However, a sucrose concentration higher than 4% is correlated well with an increase in the population of particles larger than 5 µm. It has been known that in order to achieve an effective delivery of spray-dried powders to respiratory tracts and lungs, the particle size should be smaller than 5 µm. The above results show that incorporating the carbohydrate excipient sucrose at a concentration no greater than 4% can produce a MBL powder composition with particle sizes effective for inhalation.

The shapes of the spray-dried MBL powder compositions produced in the presence of various carbohydrate concentrations were observed with a scanning electron microscope (JSM-5400, JEOL, Tokyo, Japan). As shown in FIGS. 12A to 12D, and 13A to 12E, the shapes of the spray-dried MBL powder compositions approached a more globular shape as more carbohydrate was added. The particle size also increases along with carbohydrate concentration, as confirmed by electron microscopy. The results of MBL activities, particle sizes and shapes together suggest that suitable concentrations of sucrose and lactose excipients are in the range of 1 to 2% for producing a MBL powder composition for effective inhalation.

TABLE 3

Particle Size Distribution of the Spray-dried MBL Powder Compositions at Various Sucrose Concentrations

| Carbohydrate Concentrations | DV0.1 (μm) | DV0.9 (μm) | Mean ± S.D. (μm) |
|---|---|---|---|
| 0.5% Sucrose | 2.28 | 5.32 | 3.52 ± 1.22 |
| 1.0% Sucrose | 2.68 | 9.56 | 5.83 ± 2.71 |
| 2.0% Sucrose | 2.38 | 7.49 | 4.64 ± 2.03 |
| 4.0% Sucrose | 2.94 | 12.21 | 7.07 ± 3.61 |
| 8.0% Sucrose | 2.52 | 9.98 | 5.85 ± 2.94 |

Example V

Effects of $CaCl_2$ on the Spray-Dried MBL Powder Compositions

The presence of $CaCl_2$ is essential for the activation of the complement system by MBL after binding with glycoproteins presented on the microbial surface. In general, blood $CaCl_2$ level is known to be between 5 and 10 mM. Since this concentration range corresponds to the level required for MBL activity, there is no need for additional administration of $CaCl_2$ in vascular injections. Meanwhile, when delivering MBL to such targets as respiratory tracts or lungs, MBL must be dissolved in bodily fluids of the corresponding mucosa. However, $CaCl_2$ levels in these fluids are not well understood; thus, addition of $CaCl_2$ can be contemplated in order for inhaled MBL powder formulations to be dissolved in such fluids and attain sufficient levels of biological activity.

The effects of $CaCl_2$ on the stability of and production processes for spray-dried MBL powders were investigated by evaluating the ability of the $CaCl_2$-containing MBL powder compositions to activate C4 in the complement system by using the functional MBL ELISA as described above. The MBL solutions used for spray-drying all contained 5 μg/mL recombinant MBL, 150 mM NaCl, 2% sucrose, and $CaCl_2$ at a final concentration of 10, 25, 50, 75, 100, 150 or 200 mM. When the concentration of added $CaCl_2$ was higher than 100 mM, there was no MBL powder compositions obtained suitable for inhalation. However, inhalable aerosols were obtainable in the $CaCl_2$ concentrations ranging from 10 to 50 mM. There were no significant differences among the MBL powder compositions produced from a MBL solutions containing from 10 to 50 mM $CaCl_2$.

Example VI

Effects of a Protein Excipient on the Spray-Dried MBL Powder Composition

Various protein excipients are often used for stabilizing pharmaceutical compositions of protein drugs. The effects of a protein excipient, casein, on the physical characteristics and biological stability of the spray-dried MBL powder composition is investigated by functional MBL ELISA for its biological activity, by a laser zeta potentiometer for its particle sizes and particle size distribution, and by a scanning electron microscope for its particle shapes.

Figure 14A:
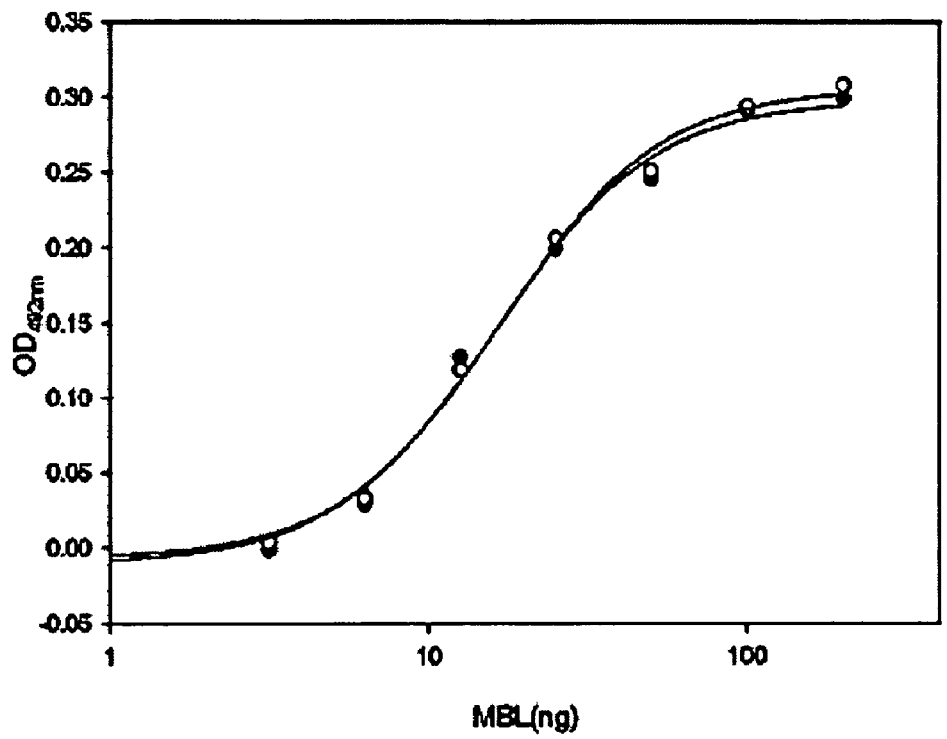
FIGS. 14 A-B compare the C4 activation levels of spray-dried MBL powder compositions (open circles) containing sucrose with (FIG. 14 A) or without casein (FIG. 14B) verses the correspondent MBL control solution (filled circles) with the same composition.
Figure 14B:
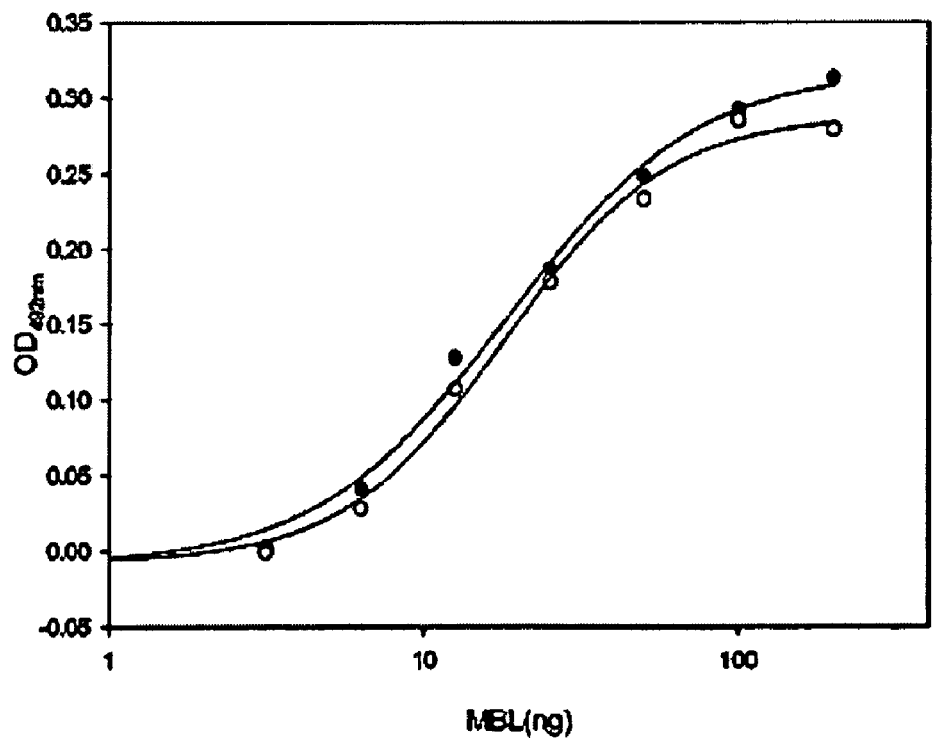
Figure 15A:
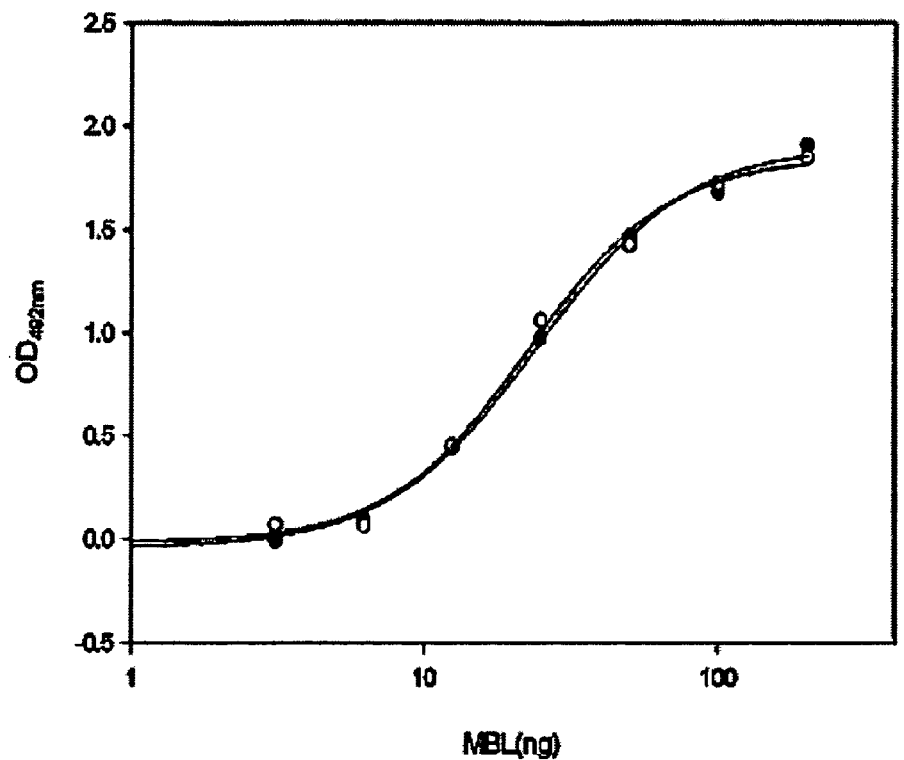
FIGS. 15 A-B compare the C4 activation levels of spray-dried MBL powder compositions (open circles) containing lactose with (FIG. 15 A) or without casein (FIG. 15B) verses the correspondent MBL control solution (filled circles) with the same composition.
Figure 15B:
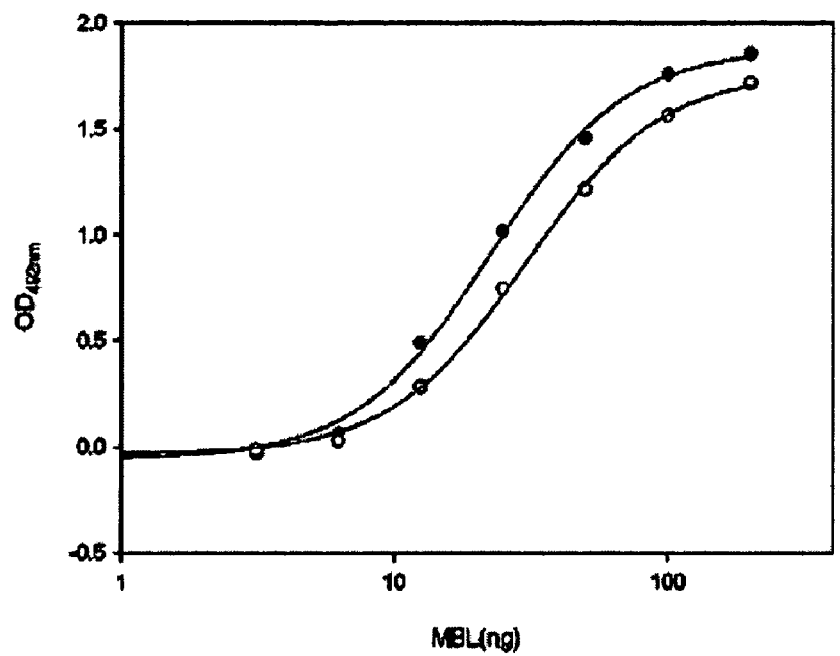

Two pairs of spray-dried MBL powder compositions were prepared. In each pair, one composition contains casein and the other does not. The first pair also contains sucrose and the results are shown in FIGS. 14A and 14B, whereas the second pair contains lactose and their results are shown in FIGS. 15A and 15B. The spray-dried MBL powder composition produced with both a carbohydrate and casein is better at maintaining C4 activation than the ones produced without casein. Casein is especially effective when the carbohydrate excipient is lactose.

In order to establish the relationship between the particle characteristics of the MBL powder compositions and casein concentrations, a series of MBL powder compositions were prepared. The initial MBL solutions used for spray-drying contained 5 μg/mL recombinant MBL, 150 mM NaCl, 10 mM $CaCl_2$, 0.8% sucrose, and casein at a final concentration of 0, 50, 200, 500, 1000, or 2000 μg/mL. The spray-dried MBL powder compositions with casein were shown to be better at maintaining their abilities for complement C4 activation than those without casein, but there is no concentration dependence observed. The particle size distributions in the MPL powder compositions are neither dependent on the presence of casein nor its concentrations. The particle sizes of the spray-dried MBL powder compositions were in the range of 2.1 to 3.1 μm, which is suitable for aerosol inhalation.

Example VII

Effects of a Polymer Excipient on the Spray-Dried MBL Powder Composition

Biodegradable polymers are widely used in the pharmaceutical formulation. The effects of a polymer excipient on spray-dried MBL powder compositions were evaluated mainly using functional MBL ELISA for C4 complement activation. Polyvinyl alcohol ("PVA"), a soluble bio-degradable polymer, was added at a final concentration of 0.05, 0.1, 0.2, 0.3 or 0.4% before drying to a series of recombinant MBL solutions, which contain 2% sucrose and 250 μg/mL casein. At PVA concentrations lower than 0.4%, C4 complement activation by spray-dried MBL powders were almost the same as those of the MBL control solutions; C4 complement activation was lower in powders compared to non-dried solutions when PVA was added to 0.4%. These results suggest that PVA, a bio-degradable polymer, is compatible as a spray-drying additive at low concentrations.

Example VIII

Determination of Storage Stability of the Spray-Dried MBL Powder Composition

Figure 16A:
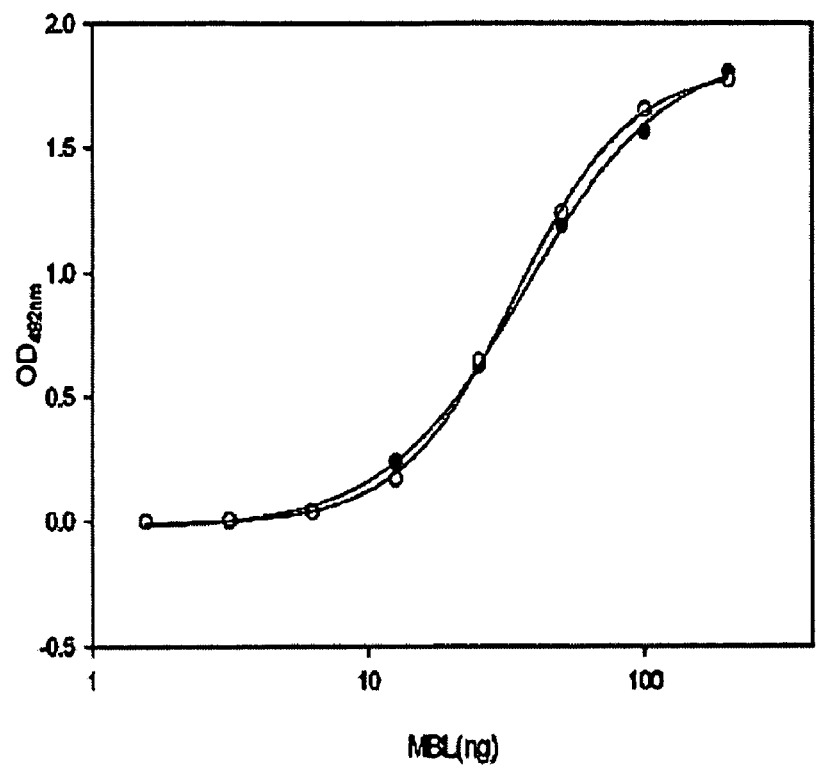
FIGS. 16 A-B compare the C4 activation levels of spray-dried MBL powder compositions (open circles) after stored at 70° C. for two days verses the same compositions stored at room temperature (filled circles). The spray-dried MBL powder composition contains either 2% lactose (16A), or 2% sucrose and 0.05% Polyvinyl Alcohol (PVA) (16B).
Figure 16B:
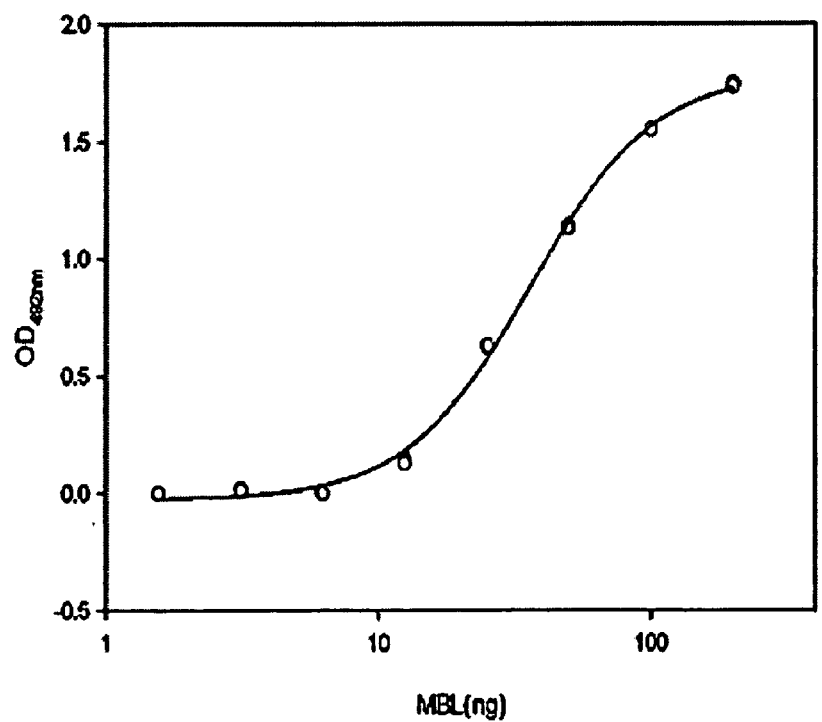
Figure 17A:
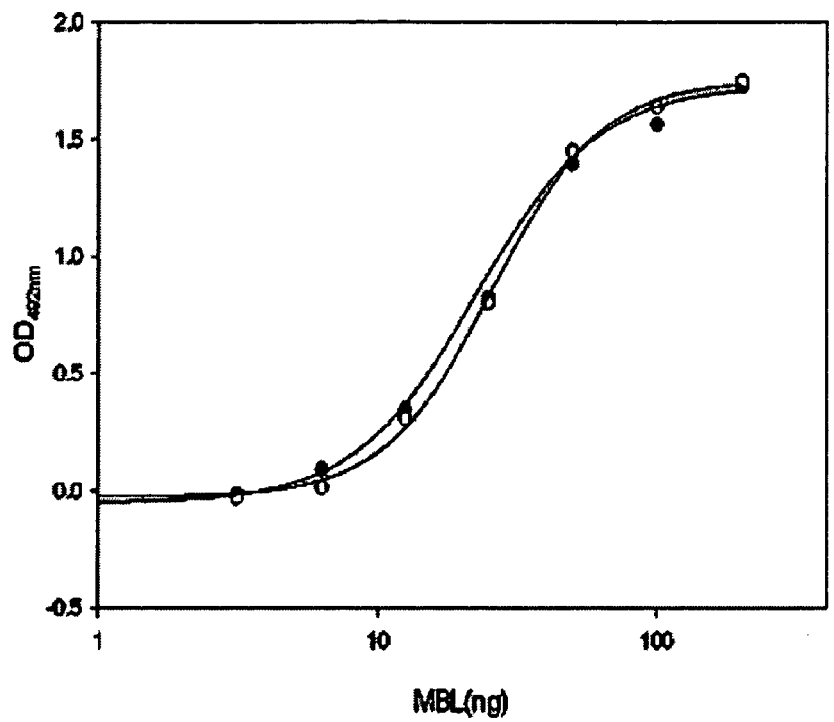
FIGS. 17 A-B compare the C4 activation levels of spray-dried MBL powder compositions (open circles) after stored at 60° C. for four days verses the same compositions stored at room temperature (filled circles). The spray-dried MBL powder composition contains either 2% lactose (16A), or 2% sucrose and 0.05% PVA (16B).
Figure 17B:
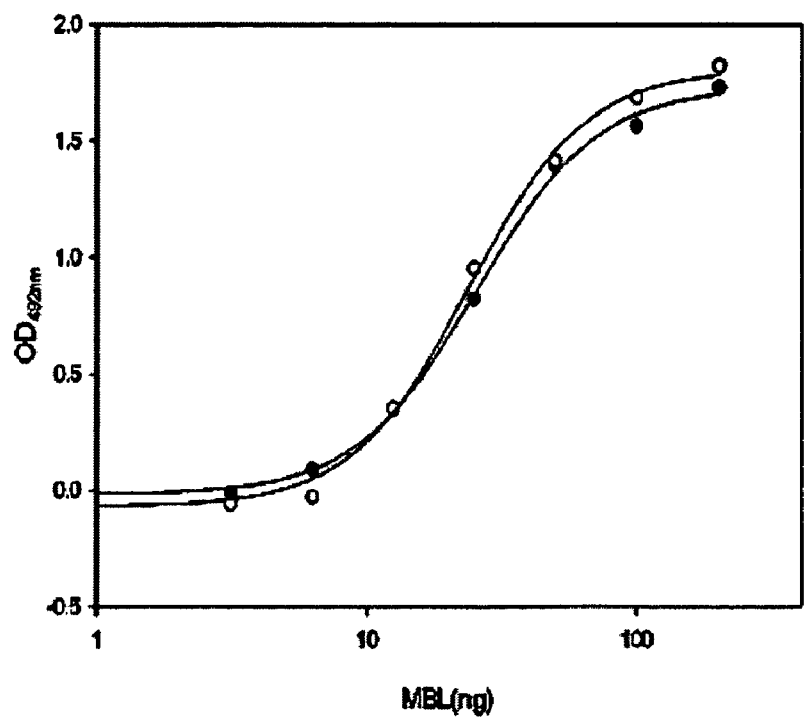

The storage stabilities of the spray-dried MBL powder compositions were evaluated by measuring their C4 complement activation under two stress storage conditions: at 70° C. for 2 days or 60° C. for 4 days, which correspond to one year-long storage at room temperature. The MBL solutions contained 5 μg/mL recombinant MBL, 150 mM NaCl, 10 mM $CaCl_2$, 0.05% PVA, and 2% lactose or sucrose. As shown in FIGS. 16 to 17, all spray-dried MBL powder compositions tested were able to maintain their C4-activating activities. At room temperature, stability was maintained 100% for one year; thus, the production method of the present invention enables formulation of MBL powders without any loss of activity, and such powders remain active for extended periods of time.

Example IX

Analysis of Binding Interactions Between the Spray-Dried MBL Powders and Microbes Since different microbes express different glycoproteins on their surfaces, MBL is expected to exhibit variations in binding affinities to different microbes. The effects of the spray-drying process of the present invention on the microbial binding affinities of the MBL powder compositions were evaluated using direct mannan-binding ELISA. Briefly, an immunoassay microplate (MAXISORP™ Immunoplate, Nunc, Denmark) were coated with microbes at $1 \times 10^7$, $1 \times 10^5$, $1 \times 10^3$, or $1 \times 10^1$ cells per well. To each well, 100 μL of MBL solutions at 5 μg/mL was added. The microplates were incubated for 2 hours at room temperature to allow binding of MBL to the oligosaccharides on the microbial surfaces. The reaction mixture was removed and the plates were washed 6 times with wash buffer. Anti-MBL antibody solution was prepared by a 10,000 fold dilution from an anti-MBL antibody stock solution (Dobeel, Korea) with a dilution buffer. The anti-MBL antibody solution (100 μL) was then added to each well and the mixture was incubated at room temperature for an hour. After removing the reaction mixture, the plates were washed 6 times with the wash buffer. Anti-mouse antibody solution (100 μL), which was prepared by a 10,000 fold dilution of an anti-mouse antibody-HRP conjugate stock solution (Kirkegaard & Perry Laboratories, USA) with a dilution buffer, was then added to each well and the reaction mixture was incubated for an 1 hour. After washing 6 times with the wash buffer, 100 μL of TMB substrate solution (KPL, USA) was added and the colorimetric reaction was allowed to proceed for 30 minutes. The reaction was stopped by adding 50 μL of 3N $H_2SO_4$. Absorbance at 450 nm was measured with an ELISA reader.

Figure 18:
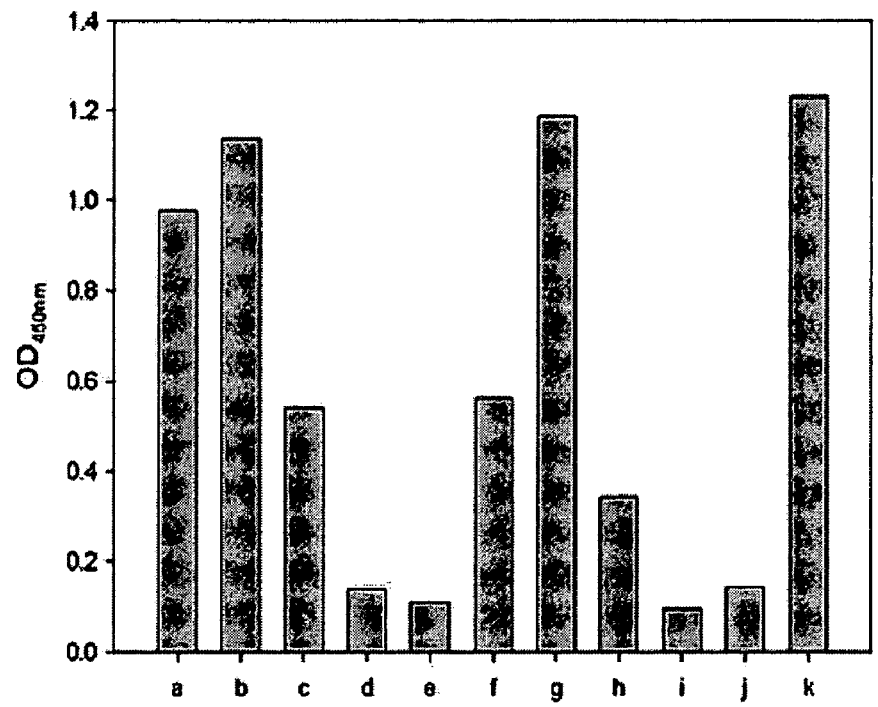
FIG. 18 shows the binding affinities of the MBL control solution towards a series of microbes as measured using direct mannan-binding enzyme-linked immunosorbent assay (ELISA). The microbes are a. *Staphylococcus aureus* ATCC29213; b, *S. aureus* CCARM3197; c, *S. aureus* CCARM3114; d, *S. epidermidis* ATCC12228; e, *S. epidermidis* CCARM35048; f, *S. pyogenes* ATCC8668; g, *Hemophilus influenzae* ATCC51907; h, *Enterococcus faecalis* ATCC51907; i, *E. faecium* CCARM5028; j, *Klebsiella pneumoniae* ATCC 10031; and k denotes *Candida alibicans*.
Figure 19:
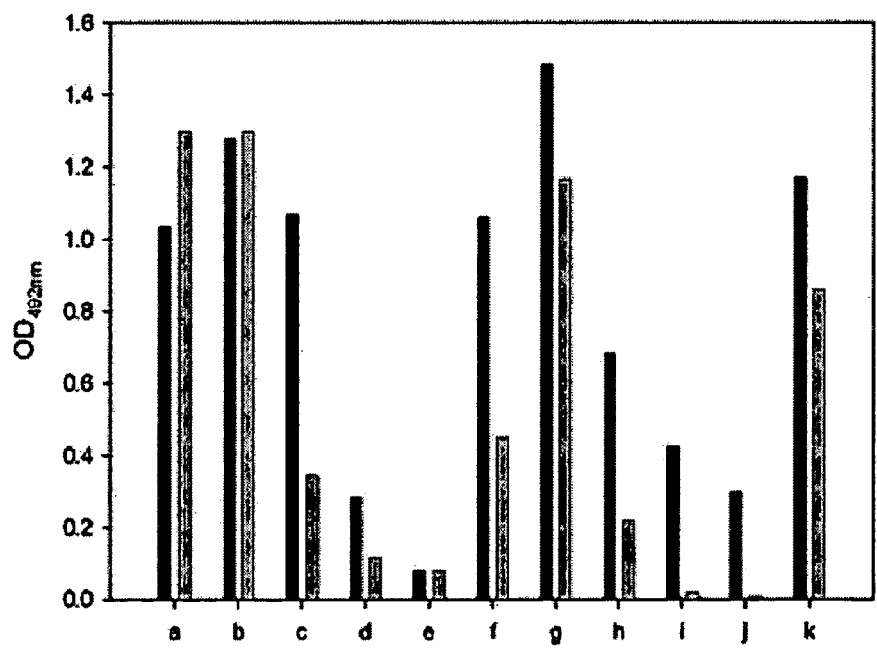
FIG. 19 shows the binding affinities of the two spray-dried MBL compositions towards a series of microbes as measured using direct mannan-binding ELISA. The first composition has 2% lactose (black) and the second has 2% sucrose and 0.05% PVA (gray). The microbes are the same as in FIG. 17B.

The dry powder MBL compositions evaluated were prepared from MBL solutions which contain 5 μg/mL recombinant MBL, 150 mM NaCl, 10 mM $CaCl_2$, 0.05% PVA, and a 2% carbohydrate excipient, lactose or sucrose. FIG. 18 compares the binding affinities of the MBL control solution towards various microbes. FIG. 19 compares the binding affinities of two spray-dried MBL powder compositions, one with 2% lactose and the other with 2% sucrose and 0.05% PVA.

As shown in FIGS. 18 and 19, the non-dried MBL solution exhibited strong binding affinities for S. aureus ATCC29213, S. aureus CCARM3197, H. influenzae ATCC51907; weak affinities for S. aureus CCARM3114 and S. pyogens ATCC8668; almost no affinity for S. epidermidis ATCC1228, S. epidermidis CCARM35048, E. faecalis ATCC51907, E. faecium CCARM5028 and K. pneumoniae ATCC 10031. Such binding behaviors were similarly repeated by the two spray-dried MBL powder compositions with excipients. Small variations in the binding are observed between spray-dried MBL powder compositions and the MBL control solutions, and between MBL preparations with different excipients, which are most likely originated from experimental errors.

* * *

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A dry powder collectin composition, comprising one or more collectins, a tonicity enhancing agent, a divalent cation salt and a carbohydrate, wherein the total content of the collectins is from about 0.001 to about 60 parts by weight, the tonicity enhancing agent content is from about 0.1 to about 10 parts by weight, the content of the divalent cation salt is from 0.1 to about 10 parts by weight, and the carbohydrate content is from about 5 to about 80 parts by weight.

2. A dry powder collectin composition comprising one or more collectin, a divalent cation salt, a tonicity enhancing agent, a carbohydrate, and a protein excipient, wherein the total content of the collectins is from about 0.001 to about 60 parts by weight, the tonicity enhancing agent content is from about 0.1 to about 10 parts by weight, the content of the divalent cation salt is from 0.1 to about 10 parts by weight, the carbohydrate content is from about 5 to about 80 parts by weight, and the content of the protein excipient is about 0.1 to about 20 parts by weight.

3. A dry powder collectin composition comprising one or more collectin, a divalent cation salt, a tonicity enhancing agent, a carbohydrate, a protein excipient, and a polymer excipient, wherein the total content of the collectins is from wherein the content of the collectin is from about 0.01 to about 20 parts by weight, the tonicity enhancing agent content is from about 8 to about 9 parts by weight, the content of the divalent cation salt is from about 1 to about 2 parts by weight, and the carbohydrate content is about 20 parts by weight, the content of the protein excipient is about 0.2 to about 2 parts by weight, and the polymer content is about 0.5 parts by weight.

* * * * *